(12) United States Patent
Kaplan

(10) Patent No.: US 7,674,829 B2
(45) Date of Patent: *Mar. 9, 2010

(54) COMPOUNDS FOR THE TREATMENT OF AIDS AND OTHER VIRAL DISEASES

(75) Inventor: Eliahu Kaplan, Ramat-HaSharon (IL)

(73) Assignee: Novaremed Limited, Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 11/089,157

(22) Filed: Mar. 24, 2005

(65) Prior Publication Data

US 2005/0239898 A1 Oct. 27, 2005

Related U.S. Application Data

(60) Provisional application No. 60/557,087, filed on Mar. 26, 2004.

(51) Int. Cl.
*A61K 31/165* (2006.01)
*C07C 233/16* (2006.01)

(52) U.S. Cl. .............. 514/617; 514/621; 564/170; 564/182

(58) Field of Classification Search .......... 564/123, 564/170, 182; 514/617, 621
See application file for complete search history.

(56) References Cited

U.S. PATENT DOCUMENTS

| 2,908,691 A | 10/1959 | Robinson .................. 260/319 |
| 4,908,322 A | 3/1990 | Jacobson et al. ............ 436/111 |
| 2006/0135620 A1 * | 6/2006 | Kaplan .................... 514/617 |

FOREIGN PATENT DOCUMENTS

| GB | 1 392 674 | 4/1975 |
| WO | WO 2004031129 A2 * | 4/2004 |

OTHER PUBLICATIONS

Beaulieu et al. *J. Med. Chem.*, 43(6):1094-1108 (2000).
Burke, Jr. et al. "Small Hydroxylated Aromatic Inhibitors of HIV-1 Integrase as Potential Anti-AIDS Drugs", NIH Conference on Retroviral Integrase Molecular and Pharmacology a Novel Target for the Treatment of Aids, pp. 1-2, XP-000980354 (1995).
Burke, Jr. et al. *J. Med. Chem.*, 38(21):4171-4178 (1995).
Hochstein, F.A., *J. Am. Chem. Soc.*,71:305-307 (1949).
Karrer et al. *Helvetica Chimica Acta*, in German, 31:1617-1623 (1948).
Repke et al. *J. Heterocyclic Chem.*, 13:7775-778 (1976).
Yasuma et al. *J. Med. Chem.*, 41:4301-4308 (1998).
Zhao et al. *J. Med. Chem.*, 40:1186-1194 (1997).

* cited by examiner

*Primary Examiner*—Rebecca L Anderson
*Assistant Examiner*—Joseph R Kosack
(74) *Attorney, Agent, or Firm*—Ivor R. Elrifi; Jennifer L. Loebach; Mintz, Levin, Cohn, Ferris, Glovsky and Popeo, P.C.

(57) ABSTRACT

The present invention provides methods for treating Acquired Immunodeficiency Syndrome (AIDS) and other viral diseases and Human Immunodeficiency Virus (HIV) related infections by administering one or more compounds of formula I:

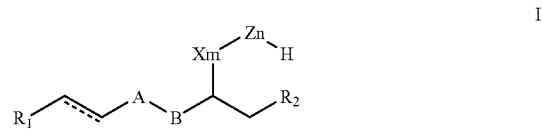

wherein:
the dotted line represents a single or a double bond; and
$R_1$ and $R_2$ are the same or different and independently of each other represent —$CH_2OH$, —$CH_2OR_4$, —$CH(OH)CH_3$, —$CH(OR_4)CH_3$ or a group represented by the formula:

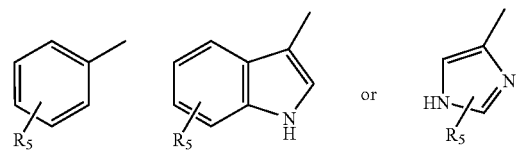

or salts or hydrates thereof in a carrier which minimizes micellar formation or van der Waals attraction of molecules of said compound. The invention also provides S enantiomeric forms of such compounds which possess the ability to inhibit cell growth whilst being of low toxicity to such cells and methods of making such compounds.

19 Claims, 17 Drawing Sheets

A

B

C

D

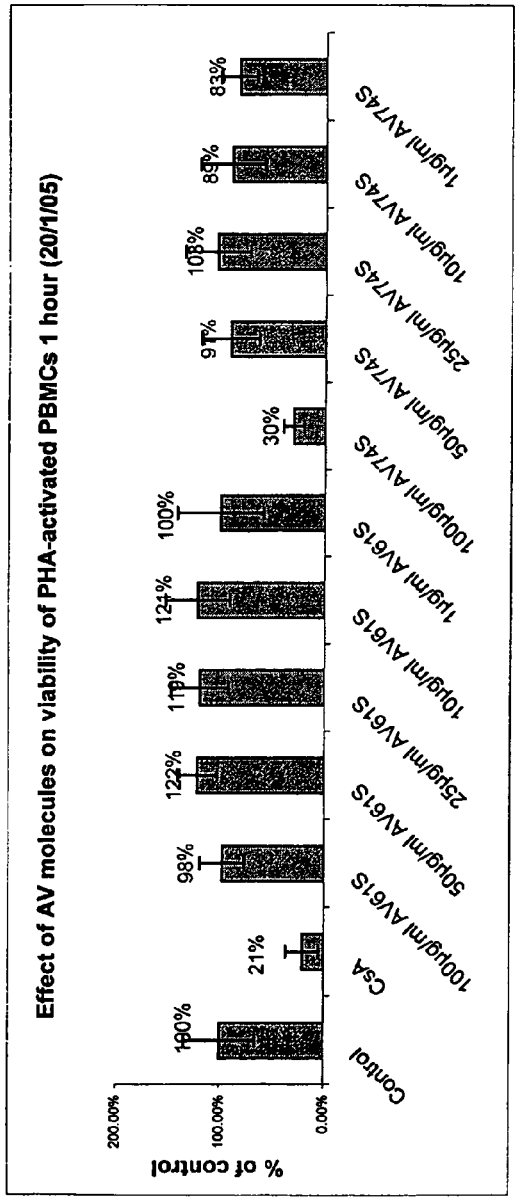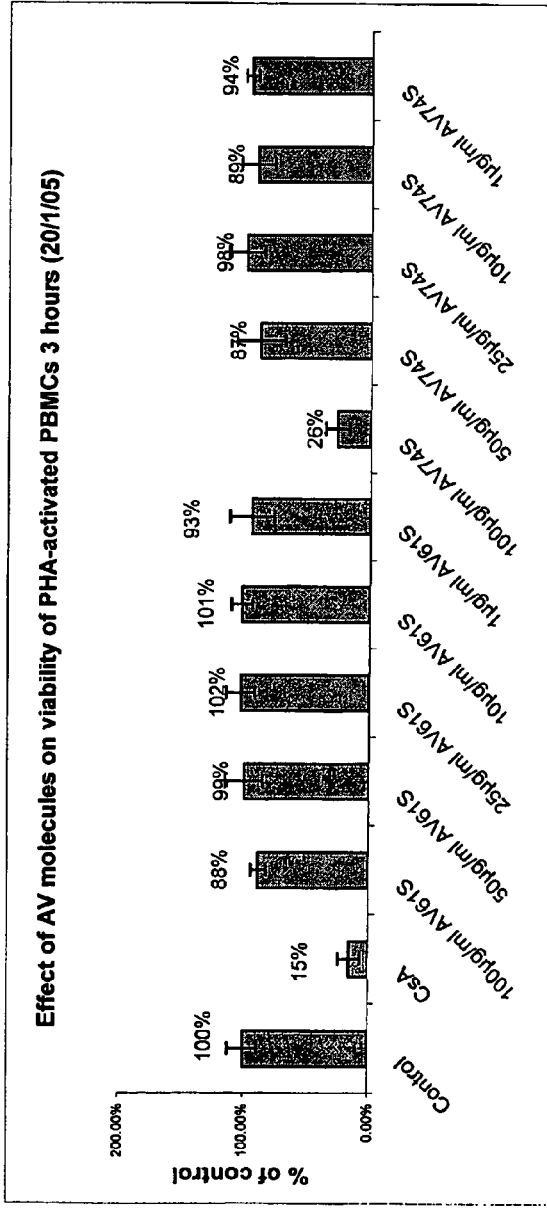

COMPOUNDS FOR THE TREATMENT OF AIDS AND OTHER VIRAL DISEASES

RELATED APPLICATIONS

This application claims the benefit of priority under 35 U.S.C. 119(e) to copending U.S. Provisional Application No. 60/557,087, filed on Mar. 26, 2004, the entire contents of which is incorporated herein by reference.

FIELD OF THE INVENTION

The present invention relates to compounds for use in the treatment of AIDS and other viral diseases and HIV+ related infections and compositions containing such compounds. The present invention also provides methods for the treatment of such diseases and infections and methods of making such compounds and compositions.

BACKGROUND OF THE INVENTION

Diseases of the immune systems pose a major threat owing to the potentially devastating effects that such diseases can have on humanity. An example of a disease of the immune system is Acquired Immunodeficiency Syndrome (AIDS). A retrovirus designated human immunodeficiency virus (HIV) is the etiological agent of AIDS, a complex disease that includes the progressive destruction of the immune system and degeneration of the central and peripheral nervous system. AIDS is one of the deadliest diseases to have struck humans in recent times, and it has reached epidemic proportions. It is estimated that over eighteen million people are infected with HIV worldwide. AIDS has been reported in more than one hundred and twenty-three countries.

Currently, a number of drugs and drug combinations are available to treat and control AIDS. There is an ongoing search in to identify potent compounds that are effective against AIDS and HIV+ related infections. Representative examples of methods and compounds for treating and controlling AIDS are disclosed in, e.g., U.S. Pat. Nos. 6,180,634; 6,120,772; 6,040,434; 6,015,796; 5,905,077; 5,888,511; 5,846,978; 5,811,462; 5,747,540; 5,744,906; 5,631,088; 5,504,065; 5,491,166; 5,475,136; 5,430,064; 5,413,999; 5,229,368; 5,162,499; 5,108,993; 5,059,592 and 5,028,995.

Diseases of the immune system pose a major problem to society. Epidemiological statistics relating to AIDS and other viral diseases show an ever increasing prevalence of such diseases, with global and regional health organizations predicting catastrophic consequences on a mass scale unless effective and easily applicable means are provided and implemented for the control of such diseases.

Accordingly there is a need in the art to develop potent compounds that are effective in the treatment, prevention and control of AIDS and other viral diseases and HIV+ related infections.

SUMMARY OF THE INVENTION

The present invention provides improvements in or relating to compounds for use in the treatment of AIDS and other viral diseases and HIV+ related infections and the like and compositions comprising such compounds. The present invention also provides methods for making such compounds and compositions and methods of treating or controlling such diseases or infections.

According to one aspect of the present invention therefore there is provided a method of treating, preventing or controlling a viral disorder by administering to a patient in need thereof a compound represented by the structure of formula I:

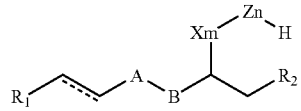

wherein:

the dotted line represents a single or a double bond.

In some embodiments, $R_1$ and $R_2$ may be the same or different and independently of each other may represent —$CH_2OH$, —$CH_2OR_4$, —$CH(OH)CH_3$, —$CH(OR_4)CH_3$ or a group represented by the formula:

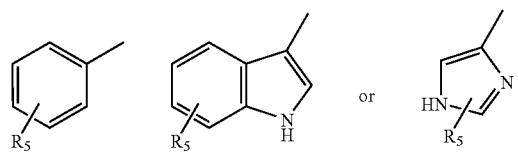

where $R_4$ is a linear or branched $C_1$-$C_4$ alkyl; $R_5$ is H, OH or $OR_6$ (where $R_6$ is a linear or branched $C_1$-$C_4$ alkyl); and A-B is a group represented by the formula:

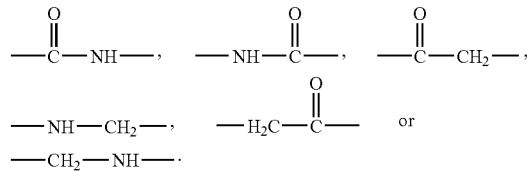

In some embodiments, m may be an integer of 0 or 1, n may be an integer of 1-500, and X may be O, —$CH_2O$, —$CH_2CH_2O$, —$CH(CH_3)CH_2O$ or —$CH_2CH(CH_3)O$.

Alternatively, m may be 1, n may be an integer of 0 to 500, and X may be —$CH_2O$, —$CH_2CH_2O$, —$CH(CH_3)CH_2O$ or —$CH_2CH(CH_3)O$.

Z may be —$CH_2CH_2O$, —$CH(CH_3)CH_2O$ or —$CH_2CH(CH_3)O$.

In some embodiments, n may be an integer of from 1-200, particularly 1-100.

Thus, in particular, X may be O, —$CH_2O$, —$CH_2CH_2O$, —$CH(CH_3)CH_2O$ or —$CH_2CH(CH_3)O$, Z may be —$CH_2CH_2O$, —$CH(CH_3)CH_2O$ or —$CH_2CH(CH_3)O$, m may be 0 or 1 and n may be 0-50, but preferably m and n may not both be 0. More preferably, n may be an integer of from 1-50.

In some embodiments, n may be an integer of from 5-75. For example, n may be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is 7, 12, 17, 34 or 69.

In some embodiments, $R_1$ may be —$CH_2OH$, —$CH_2OR_4$, —$CH(OH)CH_3$ or —$CH(OR_4)CH_3$.

Alternatively, $R_1$ may be:

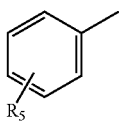

wherein $R_5$ is H or OH. Thus, in some embodiments, $R_1$ may be phenyl or:

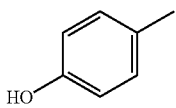

In some embodiments, $R_2$ may be —$CH_2OH$, —$CH_2OR_4$, —$CH(OH)CH_3$ or —$H(OR_4)CH_3$.

Alternatively, $R_2$ may be:

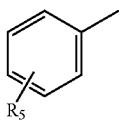

wherein $R_5$ is H or OH. Thus, in some embodiments, $R_2$ may be phenyl or

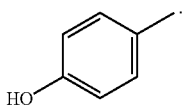

In a further aspect of the present invention there is therefore provided a method of treating, preventing or controlling a viral disorder by administering to a patient in need thereof a compound represented by the structure of formula II:

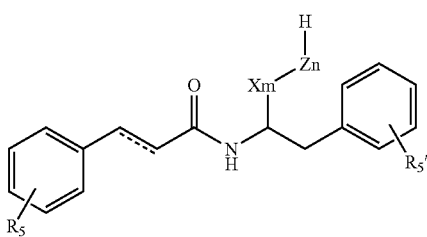

wherein:

the dotted line represents a single or a double bond; and $R_5$ and $R_5'$, independently of each other, are H, OH or $OR_6$ (where $R_6$ is a linear or branched $C_1$-$C_4$ alkyl).

As before, m may be an integer of 0 or 1, n may be an integer of 1-500, and X may be O, —$CH_2O$, —$CH_2CH_2O$, —$CH(CH_3)CH_2O$ or —$CH_2CH(CH_3)O$.

Or m may be 1, n may be an integer of 0 to 500, and X may be —$CH_2O$, —$CH_2CH_2O$, —$CH(CH_3)CH_2O$ or —$CH_2CH(CH_3)O$.

Z may be —$CH_2CH_2O$, —$CH(CH_3)CH_2O$ or —$CH_2CH(CH_3)O$.

In some embodiments, n may be an integer of from 1-200, particularly 1-100.

Thus, in particular, X may be O, —$CH_2O$, —$CH_2CH_2O$, —$CH(CH_3)CH_2O$ or —$CH_2CH(CH_3)O$, Z may be —$CH_2CH_2O$, —$CH(CH_3)CH_2O$ or —$CH_2CH(CH_3)O$, m may be 0 or 1 and n may be 0-50, but preferably m and n may not both be 0. More preferably, n may be an integer of from 1-50.

In some embodiments, n may be an integer of from 5-75. For example, n may be 5, 6, 7, 8, 10, 11, 12, 13, 15, 16, 17, 18, 20, 25, 30, 33, 34, 35, 40, 45, 50, 60, 65, 68, 69, 70, or 75. Preferably, n is 7, 12, 17, 34 or 69.

In some embodiments, m may be 0. Alternatively, X may be —$CH_2O$, and m may be 1.

Thus, the present invention comprehends methods of treating, preventing or controlling a viral disorder by administering to a patient in need thereof a compound represented by the structure of formula III:

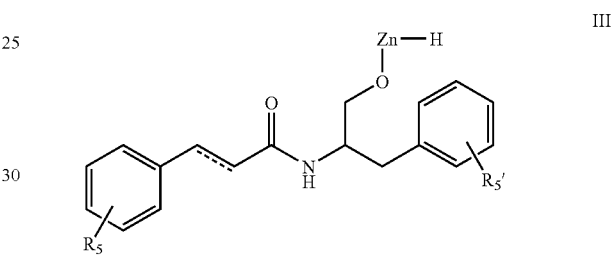

wherein the dotted line, $R_5$, $R_5'$, Z and n have the same meanings as recited above in relation to formulae I and II.

In some embodiments, Z may be —$CH(CH_3)CH_2O$, and accordingly the present invention embraces methods of treating, preventing or controlling a viral disorder by administering to a patient in need thereof a compound represented by the structure of formula IV:

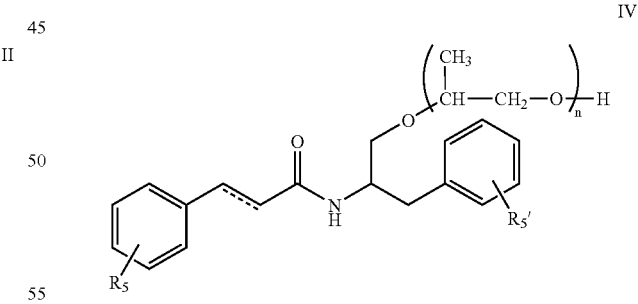

wherein the dotted line, $R_5$, $R_5'$ and n have the meanings as ascribed to them above in relation to formulae I and II.

In some embodiments, $R_5$ is H. In some embodiments, $R_5$ is OH.

In some embodiments, $R_5'$ is H. In some embodiments, $R_5'$ is OH.

In some embodiments, n is an integer of 1-20. In some embodiments, n is an integer of 10-20. In some embodiments, n is 17. Alternatively, n may be an integer of 1-10, preferably 5-10, e.g. n=7.

The present invention also includes salts or hydrates of the compounds represented by the structures of formulae I, II, III and IV.

In a particular aspect of the present invention, there is provided a method of treating, preventing or controlling a viral disorder by administering to a patient in need thereof a compound of formula A:

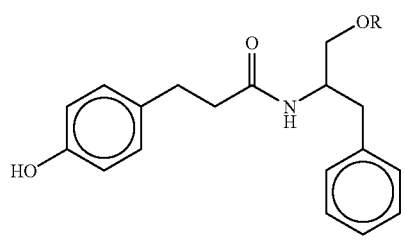

Formula A wherein R is a polyalkylene glycol polymer having p units, where p is an integer from 1-100.

In some embodiments, the polyalkylene glycol polymer may be polyisopropylene glycol.

p may be an integer of from 5-75. For example, p can be 5, 6, 7, 8, 10, 11, 12, 13, 15, 16, 17, 18, 20, 25, 30, 33, 34, 35, 40, 45, 50, 60, 65, 68, 69, 70 or 75. Preferably, p is 7, 12, 17, 34 or 69.

Further, the present invention provides methods of treating, preventing or controlling a viral disorder by administering to a patient in need thereof compounds of formulae B, C, D, E or F:

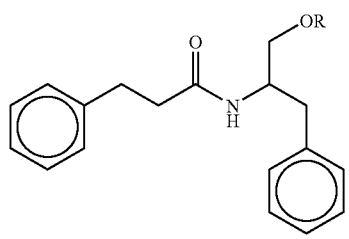

Formula B

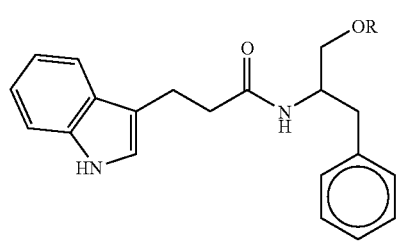

Formula C

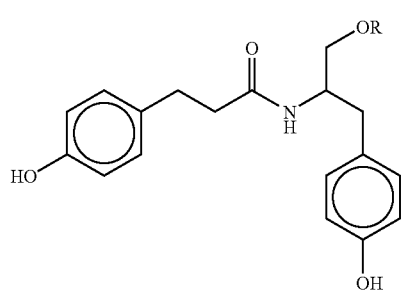

Formula D

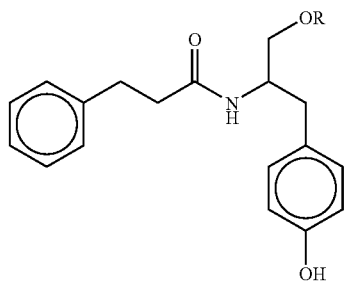

Formula E

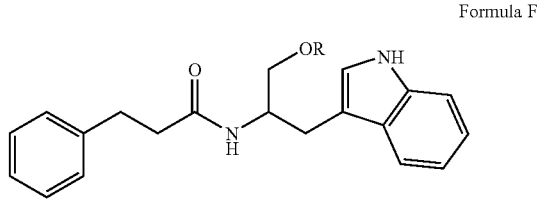

Formula F wherein R and p have the same respective meanings as given in relation to formula A.

In a different aspect of the present invention there is provided a composition for treating, preventing or controlling a viral disorder comprising one or more compounds of formulae I, II, III, IV, A, B, C, D, E or F. Thus, in some embodiments, the present invention provides a pharmaceutical composition for treating, preventing or controlling a viral disorder comprising as an active ingredient one or more compounds of formulae I, II, III, IV, A, B, C, D, E or F, together with one or more pharmaceutically acceptable excipients or adjuvants. In some embodiments, the pharmaceutical composition of the invention may comprise one or more compounds of formulae I or II.

In another aspect of the present invention there is provided a method for the treatment, prevention or control of AIDS and other viral diseases and HIV+ related infections, which method comprises administering one or more compounds of formulae I, II, III, IV, A, B, C, D, E or F and/or a pharmaceutical composition comprising one or more compounds of formulae I, II, III, IV, A, B, C, D, E or F to a patient in need thereof. Typically, one or more compounds of formulae I or II may be used.

In yet another aspect, the present invention comprehends the use of one or more compounds of formulae I, II, III, IV, A, B, C, D, E or F as hereinbefore defined in the manufacture of a medicament for the treatment, prevention or control of AIDS and other viral diseases and HIV+ related infections.

In yet another aspect of the present invention there are provided methods for inducing AICD, inducing apoptosis, inhibiting a chemokine receptor, inhibiting malignant metastasis or inhibiting fibrosis or aberrant fibroblast proliferation, which methods each comprise administering one or more compounds of formulae I, II, III, IV, A, B, C, D, E or F and/or a pharmaceutical composition comprising one or more compounds of formulae I, II, III, IV, A, B, C, D, E or F to a patient in need thereof. In some embodiments, one or more compounds of formulae I or II are used. Said compounds of the invention may suitably be administered in a carrier which minimises micellar formation or van der Waals attraction of molecules of the compounds; an example of such a carrier is DMSO.

In some embodiments, the compounds of the present invention may exclude N-cinnamoyl-D,L-phenylalaninol, N-[1-hydroxymethyl-2-(1H-indol-3-yl)-ethyl]-3-phenyl-propionamide, N-[1-hydroxymethyl-2-phenyl-ethyl]-3-(4-hydroxy-phenyl)-propionamide, N-(1-hydroxymethyl-2-phenyl-ethyl)-3-(1H-indol-3-yl)-propionamide, N-(1-hydroxymethyl-2-phenyl-ethyl)-3-phenyl-propionamide, N-[1-hydroxymethyl-2-(4-hydroxyphenyl)-ethyl]-3-phenyl-propionamide, or N-[1-hydroxymethyl-2-(1H-imidazol-4-yl)-ethyl]-3-(4-hydroxyphenyl)-propionamide.

In accordance with a different aspect of the present invention, the S-enantiomeric forms of the compounds of formulae A to F may be particularly advantageous in that embodiments thereof have been found to exhibit useful cell division inhibitory properties whilst at the same time demonstrating little or no toxicity to animal cells at the concentration levels required to achieve such cell inhibition.

Accordingly, in a particular aspect of the present invention there is provided a compound of formula A', B', C', D', E' or F' as follows:

Formula A'
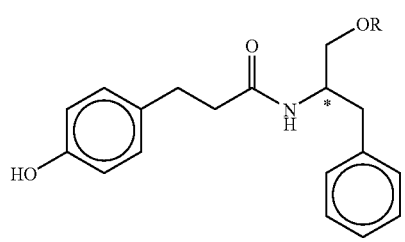

Formula B'
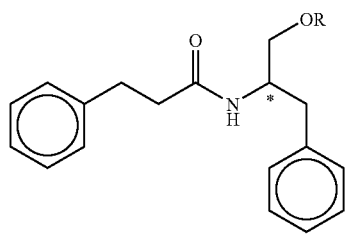

Formula C'
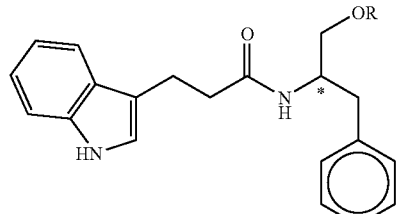

Formula D'
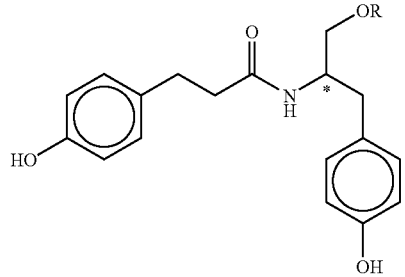

-continued

Formula E'
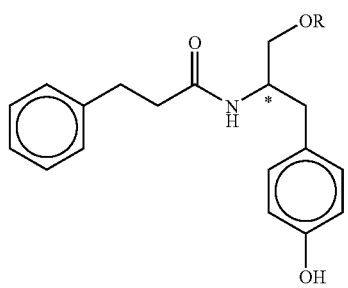

Formula F'
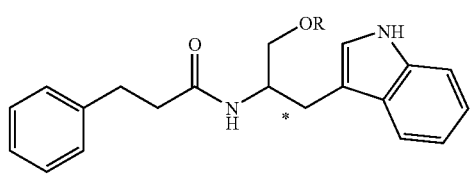

wherein the chiral centre indicated by * is in the S-enantiomeric conformation, and R represents a polyalkylene glycol polymer having p units, in which p is an integer from 1-100. Preferably R is polyethylene glycol or polypropylene glycol and p is an integer in the range 1 to 20. Particularly preferred are compounds where p is 7 or 17.

In a particular aspect of the present invention are provided (S) 2-N (3-O-polypropyleneglycol)propylbenzene)-3-(4-hydroxyphenyl) propylamide (AV 61S, p=7) and (S) 2-N (3-O-(polypropyleneglycol)-1-propyl-4-hydroxybenzene)-3-phenylpropylamide (AV 74S, p=7).

Said compounds of formula A', B', C', D', E' or F' as hereinbefore defined may be used in methods of treatment of the human or animal body by therapy, for example for the treatment, prevention or control of AIDS and other viral diseases and HIV+ related infections as described above or for the treatment or prophylaxis of immuno-allergical or autoimmune diseases or for the treatment, prevention or control of organ or tissue transplantation rejection in humans or animals as described in copending PCT/IB2003/04993, the contents of which are incorporated herein by reference.

In a different aspect of the present invention is provided a method for making a compound of formula A', D' or E' as defined above which comprises:
(i) providing a compound of formula V:

V
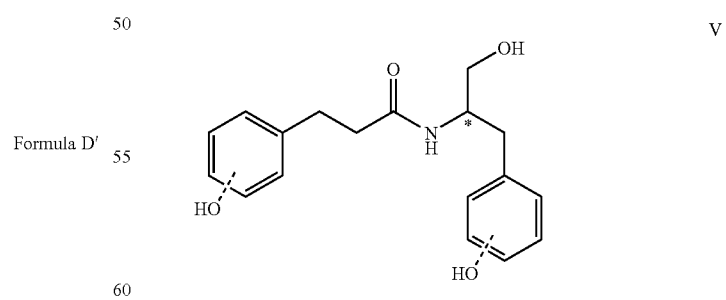

wherein the chiral centre indicated by * is the S-enantiomer, said compound of formula V comprising at least one hydroxy phenyl group;
(ii) reacting said compound of formula V with a protecting agent adapted to protect the phenylic hydroxyl group(s) on said compound;

(iii) forming an alkali metal salt of the alkyl hydroxyl group;

(iv) reacting said alkali metal salt with a polyalkylene glycol comprising a leaving group; and (v) thereafter deprotecting said phenylic hydroxyl group(s) to obtain said compound of formula A', D' or E'.

Preferably said compound of formula V comprises a phenyl group and an hydroxy phenyl group, such as a 4-hydroxy phenyl group.

Said polyalkylene glycol may be polyethylene glycol or polypropylene glycol.

A preferred protecting agent in step (ii) is di-tert-butyl dicarbonate, but any other protecting group known to those skilled in the art for use in peptide synthesis may be used.

The alkali metal salt formed in step (iii) may be the potassium or sodium salt which may be obtained, for example, by reacting the (protected) compound of formula V with sodium or potassium ethoxide.

A preferred leaving group in step (iv) is mesyl (methane sulfonyl), but other suitable leaving groups are known to those skilled in the art.

Said compound of formula V may be formed by coupling a compound of formula X:

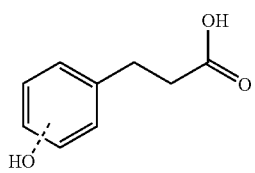

with a compound of formula Y:

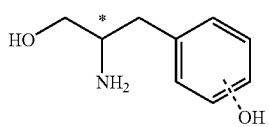

wherein at least one of X and Y comprises an hydroxy phenyl group.

In some embodiments, N-hydroxybenzotriazole (HOBt) and dicyclohexylcarbodiimide (DCC) may be employed as coupling agents, but other suitable coupling agents are known and available to those skilled in the art of peptide synthesis.

Said compound of formula X may be selected from 3-(4-hydroxyphenyl)-propionic acid and hydrocinnamic acid. Said compound of formula Y may be selected from L-tyrosinol hydrochloride and 3-(4-hydroxyphenyl)-propionic acid.

It has been found that the method for making a compound of formula A', D' or E' in accordance with the present invention gives surprisingly high yields as compared with other possible methods such, for example, as those described in copending PCT/IB2003/004993. In particular, the yield of said compound of formula A', D' or E' may be at least 20% wt. or 30% wt., with the majority of any other product(s) or residue being composed substantially of unreacted polyalkylene oxide. In some embodiments, yields of 40% wt. or more may be obtained. Generally it has been discovered that the yield of the desired compound may be greater for lower values of p. A particularly preferred value of p is 7. Another preferred value is 17.

In accordance with yet another aspect of the present invention therefore there is provided a composition comprising at least 20% wt. of a compound of formula A', D' or E', wherein R and p are as defined above. Said composition may further comprise unreacted polyalkylene glycol as a side product. In some embodiments, said composition may comprise more than about 30% wt. or 40% wt. of said compound, preferably more than 50% wt., and more preferably more than 75% wt., e.g. about 80% wt. or about 85% wt.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below by way of example only. All publications, patent applications, patents and other references mentioned herein are incorporated herein in their entirety by reference. In the case of conflict, the present specification, including definitions, will control. In addition, the materials, methods and examples are illustrative only and are not intended to be limiting.

The above description sets forth rather broadly important features of the present invention in order that the detailed description thereof that follows may be better understood and that the present contributions to the art may be better appreciated. Other objects and features of the present invention will be apparent from the following detailed description considered in conjunction with the accompanying drawings. It is to be understood that the drawings are designed solely for the purposes of illustration and not as a definition of the limits of the invention, for which reference should be made to the appended claims.

DETAILED DESCRIPTION OF THE INVENTION

Figure 1:
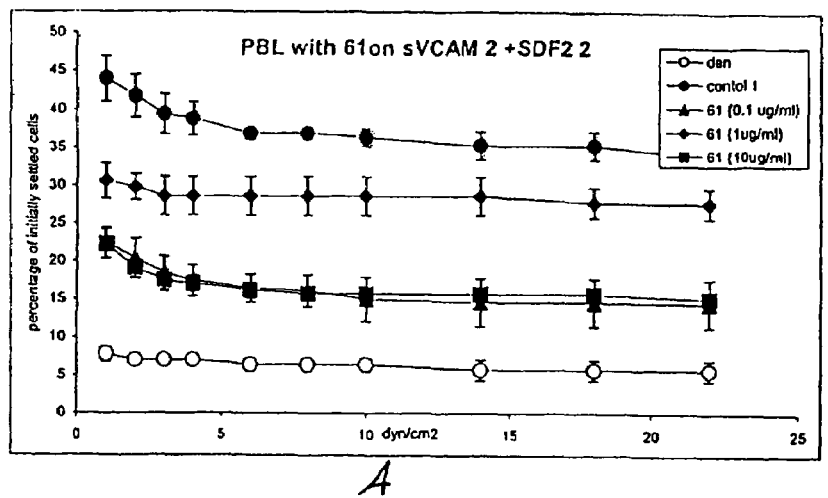
FIGS. 1-15 illustrate the data obtained from the experiments described in Examples 5-13 below.
Figure 1:
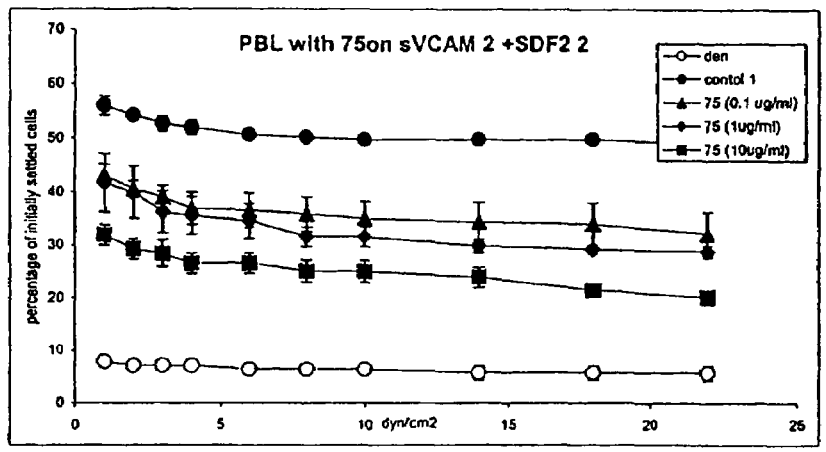
Figure 1:
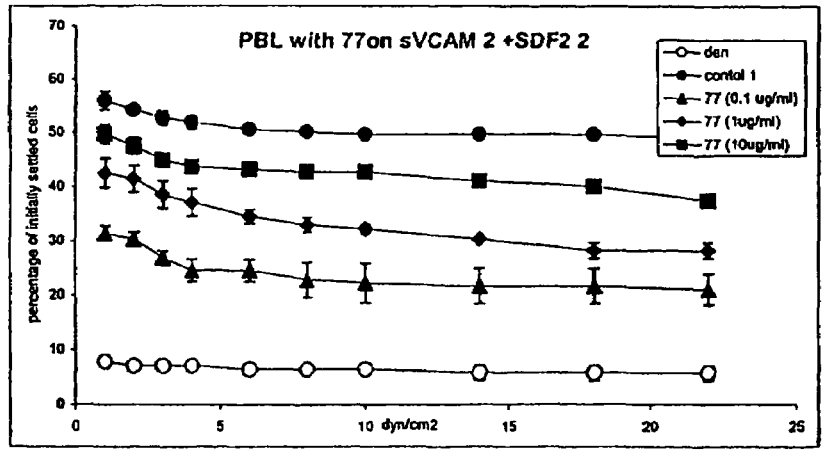
Figure 2:
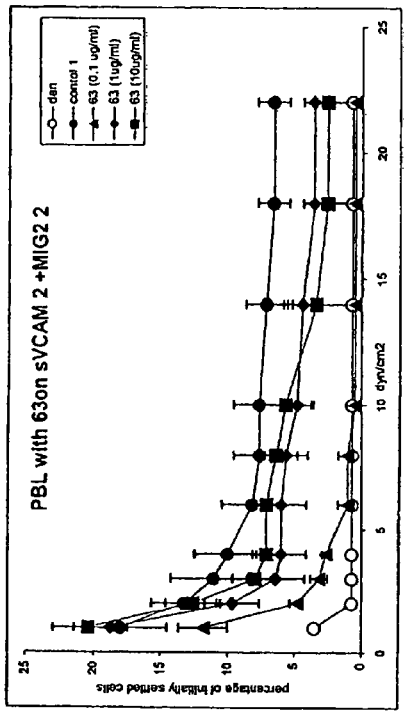
Figure 2:
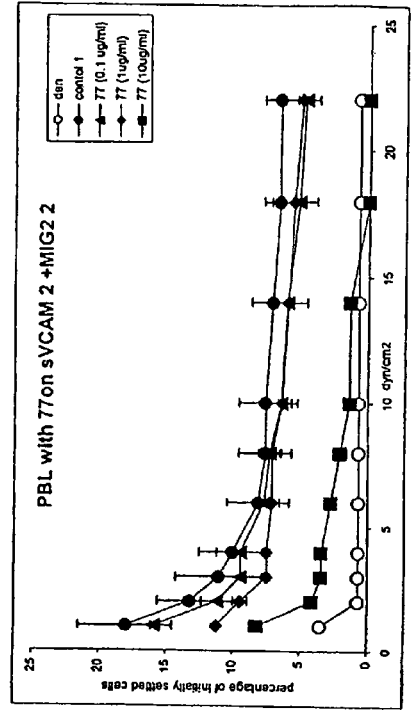
Figure 2:
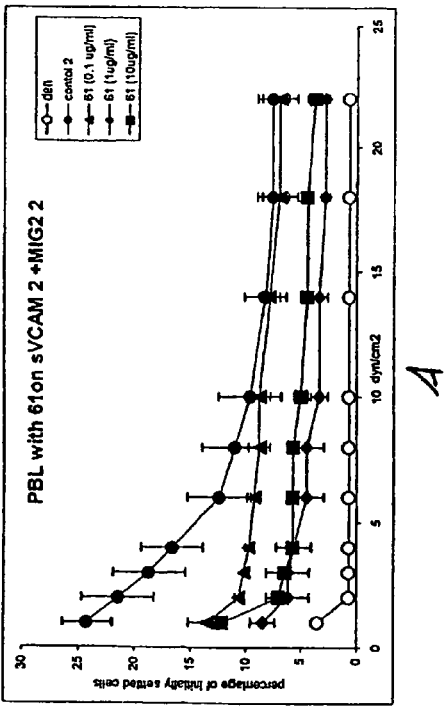
Figure 2:
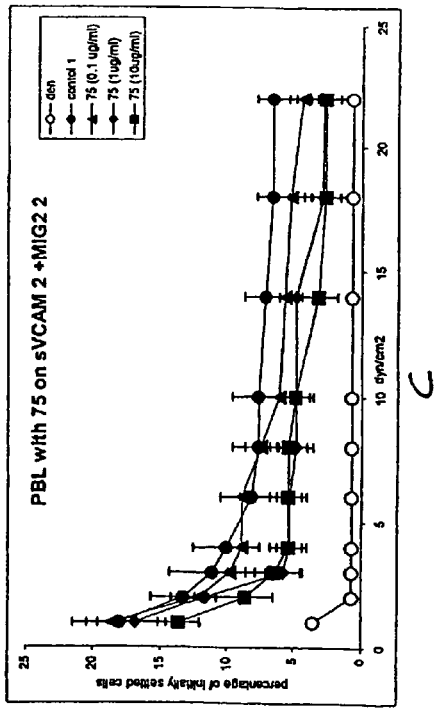

As contemplated herein, an "alkyl" group refers to a saturated aliphatic hydrocarbon, including straight-chain, branched-chain and cyclic alkyl groups. In some embodiments of the present invention, the alkyl group may have 1-4 carbons. For example, the alkyl group may be a methyl group. Alternatively, the alkyl group may be an ethyl group. Alternatively, the alkyl group may be a propyl group. Alternatively, the alkyl group may be a butyl group. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

Synthetic methodologies for obtaining the compounds of the present invention are disclosed in detail in the Examples section below. However, it should be apparent to those skilled in the art that the compounds of the present invention may be prepared by any feasible synthetic method and that, except where stated otherwise, the syntheses set forth in the Experimental Details Section are in no way limiting. Compounds of the invention may be further modified as allowed by the rules of chemistry. Such modifications include the addition of various substituents (e.g., hydroxylation, carboxylation, methylation, etc.), generation of enantiomers, creation of acid- or base-addition salts or the like. Other modifications include adding polyalkylene glycol polymers.

In accordance with the present invention the compounds of the invention may be synthesised as polyalkylene glycol (PAG) conjugates. Typical polymers used for conjugation include poly(ethylene glycol) (PEG)—also known as or poly (ethylene oxide) (PEO)— and polypropylene glycol (including poly isopropylene glycol). Such conjugates may be used to enhance solubility and stability and to prolong the blood circulation half-life of molecules.

In its most common form, a polyalkylene glycol (PAG), such as PEG, is a linear polymer terminated at each end with hydroxyl groups:

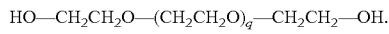
HO—$CH_2CH_2O$—$(CH_2CH_2O)_q$—$CH_2CH_2$—OH.

The above polymer, alpha-, omega-dihydroxylpoly(ethylene glycol), can also be represented as HO-PEG-OH, where it is understood that the -PEG-symbol represents the following structural unit:

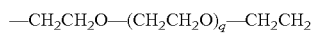
—$CH_2CH_2O$—$(CH_2CH_2O)_q$—$CH_2CH_2$ where q typically ranges from about 4 to about 10,000. PEG is commonly used as methoxy-PEG-OH, or mPEG, in which one terminus is the relatively inert methoxy group, while the other terminus is a hydroxyl group that is subject to ready chemical modification. Additionally, random or block copolymers of different alkylene oxides (e.g., ethylene oxide and propylene oxide) that are closely related to PEG in their chemistry can be substituted for PEG in many of its applications.

PAGs are polymers which typically have the properties of solubility in water and in many organic solvents, lack of toxicity and lack of immunogenicity. One use of PAGs is to attach covalently the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995).

Polyalkylated compounds of the invention may typically contain between 1 and 500 monomeric units. Other PAG compounds of the invention may contain between 1 and 200 monomeric units. Still other PAG compounds of the invention may contain between 1 and 100 monomeric units. For example, the polymer may contain 1, 10, 20, 30, 40, 50, 55, 60, 65, 70, 75, 80, 85, 90, 95, or 100 monomeric units. Some compounds of the invention may contain polymers which include between 5 and 75 or between 1 and 50 monomeric units. For example, the polymer may contain 2, 3, 5, 6, 7, 8, 10, 11, 12, 13, 15, 16, 17, 18, 20, 25, 30, 33, 34, 35, 40, 45, 50, 60, 65, 68, 69, 70, or 75 monomeric units. Preferably, m or n is 7, 12, 17, 34 or 69. The polymers may be linear or branched.

It is to be understood that compounds which have been modified by the addition of a PAG moiety may include a mixture of polymers which have a varying number of monomeric units. Typically, the synthesis of a PAG-modified compound (e.g., a PAG-conjugate) will produce a population of molecules with a Poisson distribution of the number of monomeric units per polymer in the conjugate. Thus, a compound described as having a polymer of N=7 monomeric units refers not only to the actual polymers in that population being described as having N=7 monomeric units, but also to a population of molecules with the peak of the distribution being 7. The distribution of monomeric units in a given population can be determined, e.g., by nuclear magnetic resonance (NMR) or by mass spectrometry (MS).

Throughout this application, conventional terminology is used to designate the isomers as described below and in appropriate text books known to those of ordinary skill in the art. (See, e.g., "Principles in Biochemistry", Lehninger (ed.), page 99-100, Worth Publishers, Inc. (1982) New York, N.Y.; "Organic Chemistry", Morrison and Boyd, 3rd Edition, Chap. 4, Allyn and Bacon, Inc., Boston, Mass. (1978)).

As described above, certain compounds of the present invention may exist in particular geometric or stereoisomeric forms. Except where specified to the contrary, the present invention comprehends all such compounds, including cis- and trans-isomers, R— and S— enantiomers, diastereomers, (D)-isomers, (L)-isomers, racemic mixtures thereof and other mixtures thereof as falling within the scope of the invention. Additional asymmetric carbon atoms may be present in a substituent such as an alkyl group. All such isomers, as well as mixtures thereof, are included in this invention.

A carbon atom which contains four different substituents is referred to as a chiral centre. A chiral centre can occur in two different isomeric forms. These forms are identical in all physical properties with one exception, the direction in which they can cause the rotation of plane-polarized light. These compounds are referred to as being "optically active," i.e., the compounds can rotate the plane-polarized light in one direction or the other.

The four different substituent groups attached to a carbon can occupy two different arrangements in space. These arrangements are not superimposable mirror images of each other and are referred to as optical isomers, enantiomers or stereoisomers. A solution of one stereoisomer of a given compound will rotate plane polarized light to the left and is called the levorotatory isomer [designated (−)]; the other stereoisomer for the compound will rotate plane polarized light to the same extent but to the right and is called dextrorotatory isomer [designated (+)].

The R S system was invented to avoid ambiguities when a compound contains two or more chiral centres. In general, the system is designed to rank the four different substituent atoms around an asymmetric carbon atom in order of decreasing atomic number or in order of decreasing valance density when the smallest or lowest-rank group is pointing directly away from the viewer. The different rankings are well known in the art and are described on page 99 of Lehninger. If the decreasing rank order is seen to be clock-wise, the configuration around the chiral centre is referred to as R; if the decreasing rank order is counter-clockwise, the configuration is referred to as S. Each chiral centre is named accordingly using this system.

If, for instance, a particular enantiomer of a compound of the present invention is desired, for example the S enantiomer, then it may be prepared by asymmetric synthesis or by derivation with a chiral auxiliary where the resulting diastereomeric mixture is separated and the auxiliary group cleaved to provide the pure desired enantiomers. Alternatively, where the molecule contains a basic functional group, such as an amino or acidic functional group, such as carboxyl, diastereomeric salts are formed with an appropriate optically-active acid or base, followed by resolution of the diastereomers thus formed by fractional crystallisation or chromatographic means well known in the art and subsequent recovery of the pure enantiomers.

The compositions and pharmaceutical compositions of the present invention may comprise one or more of the compounds of the present invention either in a pure form or a partially pure form. Similarly, the methods of the present invention comprise using one or more compounds, wherein the compounds are in a pure form or a partially pure form.

In some embodiments, a composition of the invention may comprise at least one of the compounds of the present invention, i.e. one or more of the compounds represented by the structures of formulae I, I, III, IV, A, B, C, D, E, F, A', B', C', D', E' and F'. In some embodiments, a composition of the invention may comprise a mixture of at least two of the compounds represented by the structures of formulae I, II, III, IV, A, B, C, D, E, F, A', B', C', D', E' and F'. In some embodiments, a composition of the invention may comprises a mixture of at least five of the compounds represented by the structures of formulae I, II, III, IV, A, B, C, D, E, F, A', B', C', D', E' or F'. In some embodiments, a composition of the invention may comprise a mixture of at least ten of the compounds represented by the structures of formulae I, II, III, IV, A, B, C, D, E, F, A', B', C', D', E' and F'.

It has been surprisingly found that one or more compounds represented by the structures of formulae I, II, III, IV, A, B, C, D, E, F, A', B', C', D', E' and F' are effective against AIDS and other viral diseases and against HIV+ related infections. Thus, in some embodiments, the present invention provides a method for the treatment, prevention or control of AIDS and other viral diseases and HIV+ related infections in human as well as in veterinary applications. In some embodiments, said method may comprise administering to a subject one or more compounds represented by the structures of formulae I, II, III, IV, A, B, C, D, E, F, A', B', C', D', E' and F'. In some embodiments, the method may comprise administering to a subject a pharmaceutical composition comprising one or more compounds represented by the structures of formulae I, II, III, IV, A, B, C, D, E, F, A', B', C', D', E' and F'.

It has also been found that compounds of the invention should be useful for treating AIDS and HIV+ related infections. In experiments described in the Examples below, compounds of the invention have shown activity in vitro. In binding experiments which involved the chemokine receptor CXCR4, compounds of the invention showed activity by preventing the function of this receptor, which is the most important receptor for the entrance of the HIV-1 T tropic into its target cell. Treatment of other conditions in which chemokine receptor inhibition is important or desirable are also contemplated. For example, control and/or prevention of malignant metastasis is highly important and desirable in cancer treatment. Since the chemokine receptor CXCR4 (and to an extent CXCR3) is involved in cell migration and is possibly the most prominent and important receptor in the movement of the malignant cells, compounds of the invention, which prevent the function of this receptor, may contribute to control/prevent the movement of such cells.

Compounds of the invention are also intended for inducing apoptosis and/or inducing AICD. The inventors have found that compounds of the invention exert an inhibitory effect under certain conditions against apoptosis, as described in PCT/IB03/04993 cited above. According to PCT/IB03/04993, however, the compounds are administered in a more hydrophilic carrier, e.g., a water-containing carrier. It has now been surprisingly found that the compounds of the invention, when dissolved in even a small amount of a carrier which minimizes micellar formation or van der Waals attraction of molecules of the compounds, like DMSO, appear to enhance the development of an immune response, as evidenced by enhanced lymphocyte proliferation and apoptotic effect which are characteristic of activation-induced cell death (AICD.) Without wishing to be bound by theory, it is believed that the effect of the DMSO (or other agent which would interfere with micellar formation) is to allow the compounds to behave differently (i.e., proliferation followed by apoptosis) than when the compounds are in 'AV micelle' wherein proliferation is inhibited.

Methods of inhibiting fibrosis or aberrant fibroblast proliferation are also within the scope of the invention. Preventing fibrosis or aberrant fibroblast proliferation is important in treating or preventing liver cirrhosis, for example, and compounds of the invention may exert an inhibitory effect on fibroblast proliferation as shown in the Examples. As such, the compounds of the invention will have usefulness in this regard.

Methods of administration are well known to a person skilled in the art. Methods of administration include, but are not limited to, parenterally, transdermally, intramuscularly, intravenously, intradermally, intranasally, subcutaneously, intraperitoneally or intraventricularly or rectally. Methods and means of administration are known to those skilled in the art from, for example, U.S. Pat. Nos. 5,693,622; 5,589,466; 5,580,859; and 5,566,064, which are hereby incorporated by reference in their entirety.

In addition, the present invention provides a pharmaceutical composition comprising as an active ingredient one or more compounds of the present invention, together with one or more pharmaceutically acceptable excipients. As used herein, "pharmaceutical composition" means a therapeutically effective amount of one or more compounds of the present invention together with suitable excipients and/or carriers useful for the treatment of immuno-allergical diseases, autoimmune diseases and organ or tissue transplantation rejection. A "therapeutically effective amount" as used herein refers to that amount that provides a therapeutic effect for a given condition and administration regimen. Such compositions can be administered by any one of the methods listed hereinabove.

A further aspect of the invention comprehends a compound of the invention in combination with other compounds of the invention. A compound of the invention may also be administered in combination with an anti-inflammatory agent, an immunosuppressant, an antiviral agent or the like. Furthermore, the compounds of the invention may be administered in combination with a chemotherapeutic agent such as an alkylating agent, anti-metabolite, mitotic inhibitor or cytotoxic antibiotic as described above. In general, currently available dosage forms of the known therapeutic agents for use in such combinations will be suitable.

Combination therapy" (or "co-therapy") includes the administration of a compound of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination is typically carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present invention.

"Combination therapy" is intended to embrace administration of these therapeutic agents in a sequential manner; that is wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, oral routes, intravenous routes, intramuscular routes and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the invention and the other pharmacologically active agent may be administered to a patient simultaneously, sequentially or in combination. It will be appreciated that when using a combination of the invention, the compound of the invention and the other pharmacologically active agent may be in the same pharmaceutically acceptable carrier and therefore administered simultaneously. They may be in separate pharmaceutical carriers such as conventional oral dosage forms which are taken simultaneously. The term "combination" further refers to the case where the compounds are provided in separate dosage forms and are administered sequentially.

The compositions and combination therapies of the invention may be administered in combination with a variety of pharmaceutical excipients, including stabilising agents, carriers and/or encapsulation formulations as described herein.

In some embodiments, the compositions of the present invention are formulated as oral or parenteral dosage forms, such as uncoated tablets, coated tablets, pills, capsules, powders, granulates, dispersions or suspensions. In some embodiments, the compositions of the present invention are formulated for intravenous administration. In some embodiments, the compounds of the present invention are formulated in ointment, cream or gel form for transdermal administration. In some embodiments, the compounds of the present invention are formulated as an aerosol or spray for nasal application. In some embodiments, the compositions of the present invention are formulated in a liquid dosage form. Examples of suitable liquid dosage forms include solutions or suspensions in water, pharmaceutically acceptable fats and oils, alcohols or other organic solvents, including esters, emulsions, syrups or elixirs, solutions and/or suspensions.

Suitable excipients and carriers can be solid or liquid and the type is generally chosen based on the type of administration being used. Liposomes may also be used to deliver the composition. Examples of suitable solid carriers include lactose, sucrose, gelatin and agar. Oral dosage forms may contain suitable binders, lubricants, diluents, disintegrating agents, colouring agents, flavouring agents, flow-inducing agents, and melting agents. Liquid dosage forms may contain, for example, suitable solvents, preservatives, emulsifying agents, suspending agents, diluents, sweeteners, thickeners, and melting agents Parenteral and intravenous forms should also include minerals and other materials to make them compatible with the type of injection or delivery system chosen.

This invention is further illustrated in the Examples section which follows. This section is set forth to aid in an understanding of the invention but is not intended to, and should not be construed to, limit in any way the invention as set forth in the claims that follow thereafter.

EXAMPLES

Example 1

Synthesis of Compounds

Compounds of the present invention were synthesised and characterized as described below.

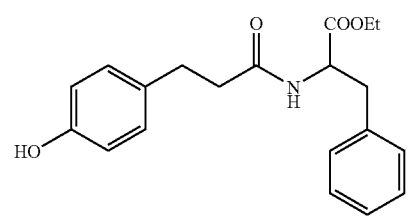

AV 23

$C_{20}H_{23}NO_4$
Mol. Wt.: 341.40

0.66 g 4 mM 4-hydroxy hydrocinnamic acid and 4 ml thionyl chloride in 30 ml cyclohexane were refluxed for 2 hours. Evaporation gave a yellow solid to which were added 0.9 g 4 mM, phenyl alanine ethyl ester HCl, 30 ml dichloromethane and 1 ml triethyl amine. After stirring 2 hours at room temperature, water and KOH were added to neutral pH and the reaction extracted with dichloromethane Evaporation gave a light yellow viscous oil, which was triturated and recrystallized with ethanol to give 0.25 g 18%, white solid, mp-213.

NMR CDCl$_3$ 7.30-6.9 (9H, m), 4.20 (2H, q, J=7.0 Hz), 3.30 (1H, m) 3.10 (2H, t, J=7.2 Hz) 2.90 (2H, m), 2.60 (2H, t, J=7.2 Hz), 1.35 (3H, t, J=7.0 Hz).

MS-341 M$^+$, 10%), 277 (15), 194 (20), 165 (M-phenethyl ester, 100%), 149 (65) m/e.

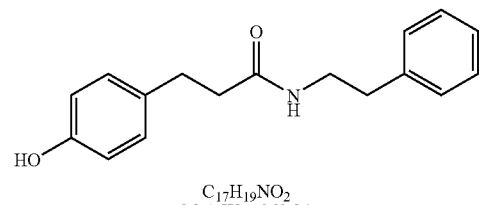

AV 24

$C_{17}H_{19}NO_2$
Mol. Wt.: 269.34

0.66 g 4 mM 4-hydroxy hydrocinnamic acid and 4 ml thionyl chloride in 30 ml cyclohexane were refluxed for 2 hours. Evaporation gave light yellow solid to which were added 0.5 g 4.1 mM, phenethyl amine, 30 ml dichloromethane and 0.6 ml triethyl amine. After stirring for 2 hours at room temperature, water and KOH were added to neutral pH and the reaction was extracted with dichloromethane. Evaporation gave a viscous oil which was recrystallized with ethanol to give 0.3 g white solid, 28%, mp-165.

NMR acetone d, 7.35-6.75 (9H, m), 3.40 (2H, q, J=7.1 Hz), 2.90 (2H, t, J=7.2 Hz) 2.75 (2H, t, J=7.2 Hz), 2.42 (2H, t, J=7.1 Hz). Phenethyl amine-NMR acetone $d_6$ 7.2 (5H, m), 2.96 (2H, t, J=7.2 Hz) 2.75 (2H, t, J=7.2 Hz).

MS-269 (M$^+$, 100%), 178 (M-benzyl) m/e.

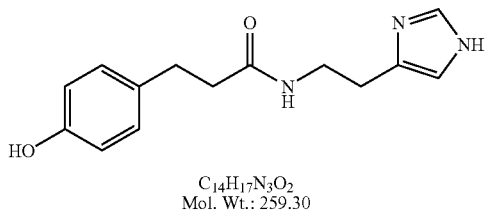

AV 26

$C_{14}H_{17}N_3O_2$
Mol. Wt.: 259.30

0.66 g 4 mM 4-hydroxy hydrocinnamic acid and 4 ml thionyl chloride in 30 ml cyclohexane were refluxed for 1.5 hours. Evaporation gave a light yellow solid to which were added 0.5 g 4.1 mM, histidine amine, 30 ml dichloromethane and 0.5 ml triethyl amine. After stirring 2 hours at room temperature, water and KOH were added to neutral pH and the reaction was extracted with dichloromethane. Evaporation gave a viscous oil which was recrystallized with ethanol to give 0.15 g white solid, 15%, mp-245.

NMR acetone $d_6$ 7.35-(6H, m), 3.42 (2H, q, J=7.1 Hz), 2.93 (2H, t, J=7.2 Hz), 2.73 (2H, t, J=7.2 Hz), 2.45 (2H, t, J=7.1 Hz).

MS-259 (M$^+$, 17%), 239 (25), 213 (18), 194 (100%), 185 (37) m/e

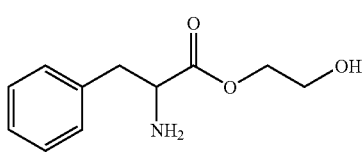

AV 27

$C_{11}H_{15}NO_3$
Mol. Wt.: 209.24

3.2 g DL phenyl alanine, 20 ml ethylene glycol and 7 ml thionyl chloride were refluxed for 2 hours. Workup as above gave 1.3 g oil which was used in the synthesis of AV 28.

NMR acetone $d_6$ 7.35-(5H, m), 4.50, 3.27, 2.90 (3H, 12 line ABX), 4.32 (2H, t, J=7.0 Hz), 3.76 (2H, t, J=7.0 Hz).

AV 28

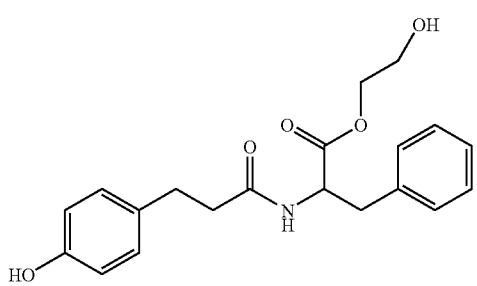

$C_{20}H_{23}NO_5$
Mol. Wt.: 357.40

1 g 6 mM 4-hydroxy hydrocinnamic acid and 5 ml thionyl chloride in 30 ml cyclohexane were refluxed for 1.5 hours. Evaporation gave a light yellow solid to which were added 1.2 g AV 27 in 30 ml dichloromethane and 1 ml triethyl amine. After stirring 2 hours at room temperature, water and KOH were added to neutral pH and the reaction was extracted with dichloromethane. Evaporation gave a viscous oil which was recrystallized with ethanol to give 0.18 g white solid, 8%, mp-224.

NMR acetone $d_6$ 7.35-6.8 (9H, m), 3.73-2.50 (12H, m).

AV 29

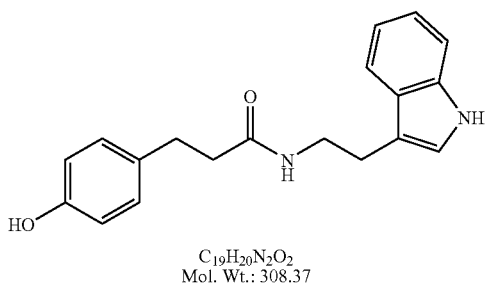

$C_{19}H_{20}N_2O_2$
Mol. Wt.: 308.37

0.22 g 1.3 mM, 4-hydroxy hydrocinnamic acid and 2 ml thionyl chloride in 30 ml cyclohexane were refluxed for 1.5 hours. Evaporation gave a light yellow solid to which were added 0.2 g 1.4 mM, tryptamine in 30 ml dichloromethane and 0.3 ml triethyl amine. After stirring 1.5 hours at room temperature, water and KOH were added to neutral pH and the reaction was extracted with dichloromethane. Evaporation gave a viscous oil which was recrystallized with ethanol to give 0.11 g white solid, 27%, mp-136.

NMR acetone $d_6$ 7.36 (2H, d, J=7.8 Hz), 7.0 (8H, m), 3.48 (2H, q, J=7.1 Hz), 3.05 (2H, t, J=7.1 Hz), 2.88 (2H, t, J=7.1 Hz), 2.52 (2H, t, J=7.1 Hz).

AV 30

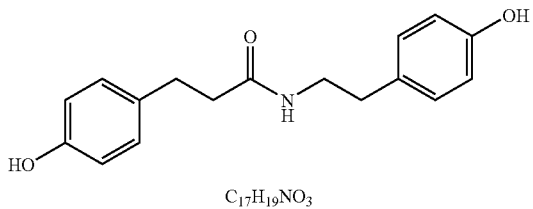

$C_{17}H_{19}NO_3$
Mol. Wt.: 285.34

0.22 g 1.3 mM, 4-hydroxy hydrocinnamic acid and 2 ml thionyl chloride in 30 ml cyclohexane were refluxed for 1.5 hours. Evaporation gave light yellow solid to which were added 0.2 g 1.5 mM, tyramine, 30 ml dichloromethane and 0.3 ml triethyl amine. After stirring for 2 hours at room temperature, water and KOH were added to neutral pH and the reaction was extracted with dichloromethane. Evaporation gave a viscous oil which was recrystallized with ethanol to give 85 mg white solid, 23%.

NMR acetone $d_6$ 7.36 (4H, ABq, J=8.8 Hz), 7.20 (4H, Abq, J=8.6 Hz), 3.48 (2H, q, J=7.1 Hz), 3.05 (2H, t, J=7.1 Hz), 2.88 (2H, t, J=7.1 Hz), 2.52 (2H, t, J=7.1 Hz).

AV 32

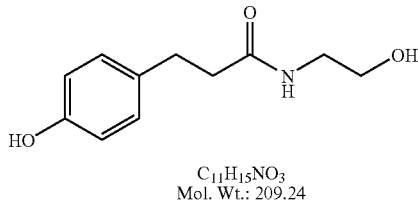

C$_{11}$H$_{15}$NO$_3$
Mol. Wt.: 209.24

A. 0.8 g 4-hydroxy cinnamic acid in 40 ml methanol and 10 drops HCl were refluxed for 12 hours. Workup as above gave 0.6 g oil, 68% yield.

NMR CDCl$_3$ 7.02, 6.75 (4H, Abq, J=8.6 Hz), 3.66 (3H, s), 2.86 (2H, t, J=7.4 Hz), 2.60 (2H, t, J=7.4 Hz).

B. 0.6 g 3.3 mM, ester from step A and 0.26 g 4.2 mM, ethanol amine were heated at 100 for 3 hours in an open vessel. Chromatography gave 0.3 g recovered ester followed by amide. The viscous oil was triturated with acetone-methylene chloride and filtered to give 160 mg white solid, 23% yield, mp-102.

NMR acetone d$_6$ 8.10 (1H, s, OH), 7.03, 6.74 (4H, Abq, J=8.8 Hz), 3.90 (1H, t, J=5.2 Hz, NH), 3.54 (2H, q, J=7.1 Hz), 3.28 (2H, t, J=7.1 Hz), 2.80 (2H, t, J=8.2 Hz), 2.41 (2H, t, J=8.2 Hz).

AV 33

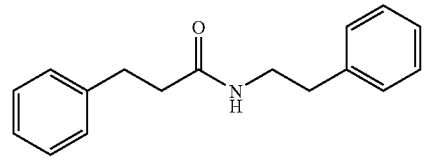

C$_{17}$H$_{19}$NO
Mol. Wt.: 253.34

0.9 g, 6 mM, hydrocinnamic acid and 0.6 g 6 equivalents, triphosgen in 30 ml dichloromethane and 1.5 ml triethyl amine were stirred 10 minutes at room temperature and 0.7 g phenethyl amine were added. After 2 hours at room temperature, workup (HCl) gave a viscous oil which was recrystallized with hexane-methylene chloride to give 166 mg white solid, 11%, mp-91.

NMR acetone d$_6$ 7.35 (10H, m), 3.40 (2H, q, J=7.2 Hz), 2.90 (2H, t, J=7.4 Hz), 2.74 (2H, t, J=7.2 Hz), 2.46 (2H, t, J=7.4 Hz).

AV 34

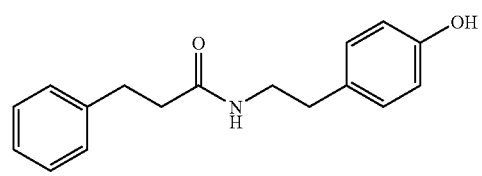

C$_{17}$H$_{19}$NO$_2$
Mol. Wt.: 269.34

Prepared as AV 33, in the same amount but with tyramine instead of phenethyl amine. Chromatography and trituration with benzene-hexane gave 220 mg white solid, 14%, mp-98.

NMR acetone d$_6$ 7.25 (5H, m), 6.96, 6.75 (4H, Abq, J=8.4 Hz), 3.43 (2H, q, J=6.8 Hz), 2.94 (2H, t, J=7.6 Hz), 2.65 (2H, t, J=6.8 Hz), 2.42 (2H, t, J=7.6 Hz).

AV 35

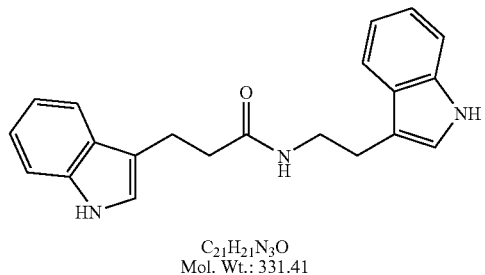

C$_{21}$H$_{21}$N$_3$O
Mol. Wt.: 331.41

Prepared as AV 33, 3 mM, from indole propionic acid and tryptamine. Chromatography and trituration with ethanol gave 162 mg white solid, 16%, mp-142.

NR acetone d$_6$ 7.57 (2H, d, J=7.8 Hz), 7.36 (2H, d, J=7.8 Hz), 7.0 (8H, m), 3.48 (2H, q, J=7.1 Hz), 3.05 (2H, t, J=7.1 Hz), 2.88 (2H, t, J=7.1 Hz), 2.52 (2H, t, J=7.1 Hz).

AV 38

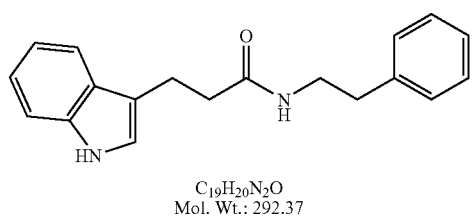

C$_{19}$H$_{20}$N$_2$O
Mol. Wt.: 292.37

Prepared as AV 33, 2 mM, from indole propionic acid and phenethyl amine. Chromatography and trituration with ethanol gave 220 mg white viscous oily solid, 37%.

NMR acetone d$_6$ 7.57 (2H, d, J=7.8 Hz)), 7.25-6.97 (9H, m), 3.44 (2H, q, J=7.1 Hz), 3.10 (2H, t, J=7.1 Hz), 2.66 (2H, t, J=7.1 Hz), 2.51 (2H, t, J=7.1 Hz).

AV 43

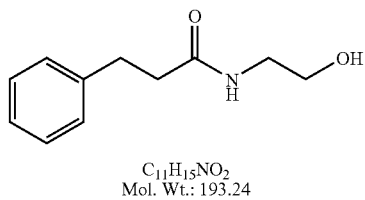

C$_{11}$H$_{15}$NO$_2$
Mol. Wt.: 193.24

0.9 g 6 mM hydrocinnamic acid and 0.6 g 6 equivalents, triphosgen in 30 ml dichloromethane and 1 ml triethyl amine were stirred for 10 minutes at room temperature and 0.6 g ethanol amine were added. After 2 hours at room temperature, workup (HCl) gave a viscous oil which was recrystallized with hexane to give 124 mg white solid, 11%, mp-91.

NMR acetone d$_6$ 7.30 (5H, m), 3.63 (2H, t, J=5.2 Hz), 3.36 (2H, q, J=5.2 Hz), 2.97 (2H, t, J=7.3 Hz), 2.50 (2H, t, J=7.3 Hz).

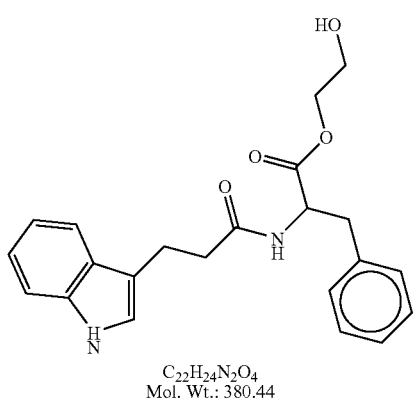

AV 45

C₂₂H₂₄N₂O₄
Mol. Wt.: 380.44

Prepared similar to AV 28, but with the triphosgen method, from 6 mM indole propionic acid, AV 27. Chromatography gave 0.35 g viscous oil, 13% yield.

NMR CDCl₃ 7.95 (1H (br.s), 7.57 (2H, d, J=8.0 Hz), 7.36-6.90 (9H, m), 4.36 (2H, t, J=7.1 Hz), 4.17 (2H, q, J=7.0 Hz), 3.5-2.8 (7H, m).

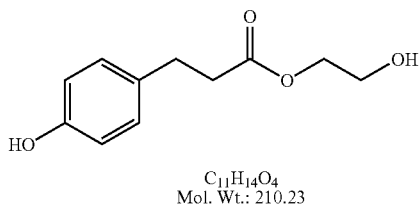

AV 46

C₁₁H₁₄O₄
Mol. Wt.: 210.23

0.65 g 3.9 mM, 4-hydroxy hydrocinnamic acid, 15 ml ethylene glycol and 5 ml thionyl chloride were refluxed 3 hours. Workup gave 0.5 g 61%, oil.

NMR acetone d₆ 7.02, 6.76 (4H, ABq, J=8.6 Hz), 4.28 (2H, t, J=7.1 Hz), 3.63 (2H, t, J=7.1 Hz), 2.85, 2.63 (4H, m).

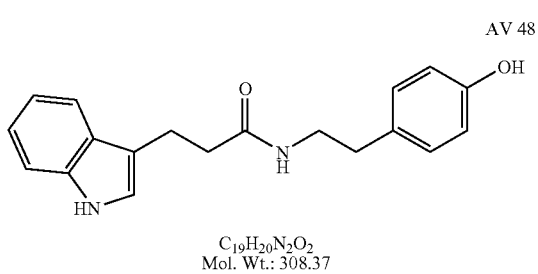

AV 48

C₁₉H₂₀N₂O₂
Mol. Wt.: 308.37

Prepared as AV 33, 3 mM, from indole propionic acid and tyramine. Chromatography and trituration with ethanol-hexane gave 120 mg pink-white solid, 13%.

NMR acetone d₆ 7.57 (2H, d, J=7.8 Hz)), 7.25-6.97 (8H, m), 3.44 (2H, q, J=7.1 Hz), 3.10 (2H, t, J=7.1 Hz), 2.66 (2H, t, J=7.1 Hz), 2.51 (2H, t, J=7.1 Hz).

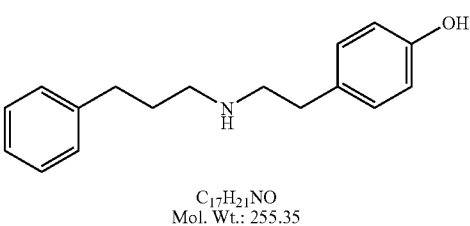

AV 49

C₁₇H₂₁NO
Mol. Wt.: 255.35

To 0.7 g 5 mM, hydrocinnamic aldehyde and 0.7 g 5 mM, tyramine in 20 ml ethanol was added 0.4 g NaBH₄ and the reaction refluxed 1 hour. Workup gave 0.7 g viscous oil, 55% yield.

NMR acetone d₆ 7.35 (5H, m), 7.15, 6.85 (4H, ABq, J=8.6 Hz), 2.85 (2H, t, J=6.7 Hz), 2.70 (6H, m), 1.80 (2H, quin., J=7.2 Hz).

Example 2

Synthesis of Polyalkylene Glycol Compounds

Polyalkylene glycol compounds were generally synthesised by preparation of the appropriate alcohol compound (e.g., one of the compounds described in Example 1, or a hydroxylated derivative thereof) and then conjugation of the alcohol with a polyalkylene glycol (PAG) polymer (e.g., polyethylene glycol (PEG) or polypropylene glycol (PPG)) of the desired length.

Compound 1, Phenyl Alaninol 1.2 g 32 mM, of LiAlH₄ were added to 2.3 g 10 mM, phenyl alanine ethyl ester HCl in 50 ml dry ether. After stirring for 2 hours at room temperature, water and KOH were added and the reaction product was extracted with ethyl acetate. After evaporation, 0.8 g of compound 1, a light yellow oil, was obtained.

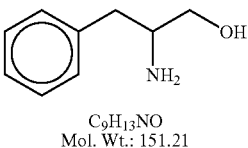

1

C₉H₁₃NO
Mol. Wt.: 151.21

Compound 1 crystallized on standing. Mp-70.

NMR CDCl₃ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz)

NMR acetone d₆ 7.30 (5H, m), 3.76 (1H, dt) 3.60 (1H, m) 3.30 (1H, t), 2.85 (2H, m).

*Helv. Chim. Acta*, 31, 1617 (1948). Biels. -E3, Vol. 13, p 1757.

Compound 2, Tyrosinol

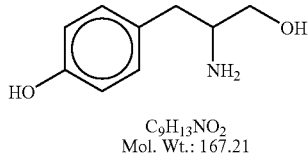

To 3 g 12 mM, L- tyrosine ethyl ester. HCl in 50 ml dry ether was added 1.2 g 32 mM LiAlH$_4$. After stirring 3 hours at room temperature, water and KOH were added and the reaction was extracted with ethyl acetate. Evaporation gave 1.1 g of a light yellow oil, 54% yield, which on standing crystallized. mp-85.

NMR CDCl$_3$ 7.20 (4H, AB q, J=8.6 Hz), 3.50 (2H, m) 3.20 (1H, m), 2.81 (2H, m).

NMR tyrosine ethyl ester free base CDCl$_3$ 7.0, 6.56 (4H, AB q, J=8.8 Hz), 4.20 (2H, q, J=7, 0 Hz), 3.70, 3.0, 2.80 (3H, 12 line ABXm), 1.28. (3H, t, J=7.0 Hz).

*JACS*, 71, 305 (1949). *Biels*. -E3, Vol. 13, p 2263.

Compound 3, Tryptophanol

To 3 g 12.9 mM, L-tryptophan methyl ester. HCl in 50 ml dry ether was added 1.2 gr, 32 mM LiAlH$_4$. After stirring 6 hours at room temperature water and KOH were added and the reaction extracted with ethyl acetate. Evaporation gave 1.23 g light yellow oil, 50% yield. On standing crystallized. Mp-65.

NMR CDCl$_3$ 7.30 (5H, m), 3.64 (1H, dd, J=10.5, 3.8 Hz) 3.40 (1H, dd, J=10.5, 7.2 Hz) 3.12 (1H, m), 2.81 (1H, dd, J=13.2, 5.2 Hz), 2.52 (1H, dd, J=13.2, 8.6 Hz)

*J. Het. Chem*, 13, 777 (1976). *Biels*. -E5, 22 Vol. 12, p 90.

Compound 4, AV 22

0.66 g 4-hydroxy hydrocinnamic acid and 4 ml thionyl chloride in 30 ml cyclohexane were refluxed for 2 hours. After evaporation, a white solid was obtained, to which 0.65 g oil of Compound 1 (4.3 mM) in 30 ml dichloromethane and 0.4 ml triethyl amine were added. After stirring for 2 hours at room temperature, water and KOH were added in order to neutralize the pH. The reaction product was extracted with dichloromethane. Evaporation gave 0.8 g of compound 4, light yellow viscous oil. Part of this product was triturated and recrystallized with ethanol to give a white solid. Mp-149.

NMR CDCl$_3$ 7.30-6.9 (9H, m), 3.50 (2H, m) 3.30 (2H, t, J=7.2 Hz) 2.90 (3H, m), 2.60 (2H, t, J=7.2 Hz).

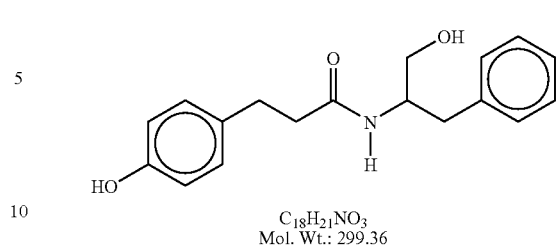

Compound 5, AV 57

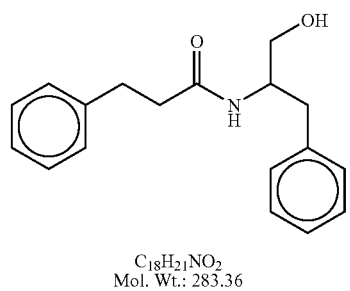

0.75 g 5 mM, hydrocinnamic acid and 4 ml thionyl chloride in 30 ml cyclohexane were refluxed for 2 hours. Evaporation gave a white solid to which were added 0.83 g 5.5 mM, phenyl alaninol in 30 ml dichloromethane and 0.5 ml triethyl amine. After stirring 3 hours at room temperature, water and KOH were added to neutral pH and the reaction was extracted with dichloromethane. Evaporation gave 0.57 g of a yellow viscous oil, 40% yield.

NMR CDCl$_3$ 7.40-7.10 (10H, m), 3.60 (2H, m) 3.35 (2H, t, J=7.2 Hz) 2.95 (3H, m), 2.50 (2H, t, J=7.2 Hz).

Compound 6, AV 58

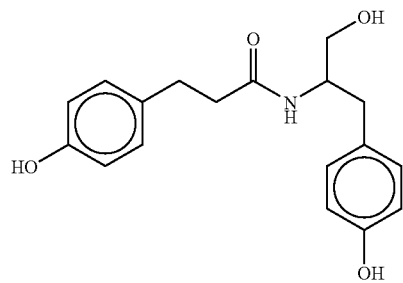

0.66 g 4 mM, 4-hydroxy hydrocinnamic acid and 4 ml thionyl chloride in 30 ml cyclohexane were refluxed 3 hours. Evaporation gave a light yellow solid to which were added 0.72 g 4.3 mM, tyrosinol in 30 ml dichloromethane and 0.5 ml triethyl amine. After stirring 3 hours at room temperature. water and KOH were added to neutral pH and the reaction was extracted with dichloromethane. Evaporation gave 0.53 g light yellow viscous oil, 42% yield.

NMR CDCl$_3$ 7.30, 7.20 (8H, 2 ABq, J=8.6 Hz), 3.40 (2H, m) 3.30 (2H, t, J=7.2 Hz) 2.90 (3H, m), 2.60 (2H, t, J=7.2 Hz).

Compound 7 AV 59

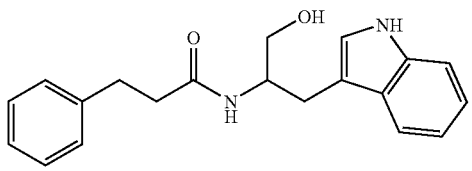

C₂₀H₂₂N₂O₂
Mol. Wt.: 322.40

0.45 g 3 mM, hydrocinnamic acid and 3 ml thionyl chloride in 30 ml cyclohexane were refluxed for 2 hours. Evaporation gave a light yellow solid to which were added 0.66 g 3.5 mM, tryptophanol in 30 ml dichloromethane and 0.4 ml triethyl amine. After stirring 3 hours at room temperature, water and KOH were added to neutral pH and the reaction was extracted with dichloromethane. Evaporation gave 0.61 g viscous oil, 63% yield.

NMR CDCl₃ 7.50-7.05 (10H, m), 3.65 (2H, m) 3.32 (2H, t, J=7.3 Hz) 2.92 (3H, m), 2.53 (2H, t, J=7.3 Hz).

Compound 8, AV 72

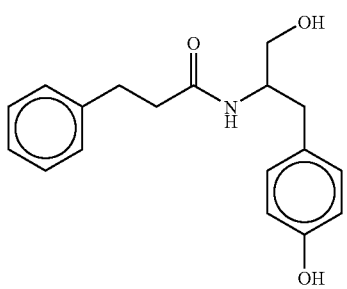

C₁₈H₂₁NO₃
Mol. Wt.: 299.36

0.45 g 3 mM, hydrocinnamic acid and 3 ml thionyl chloride in 30 ml cyclohexane were refluxed for 2 hours. Evaporation gave a light yellow solid to which were added 0.58 g 3.5 mM, tyrosinol in 30 ml dichloromethane and 0.4 ml triethyl amine. After stirring for 2.5 hours at room temperature, water and KOH were added to attain neutral pH and the reaction was extracted with dichloromethane. Evaporation gave 0.57 g light yellow viscous oil, 63% yield.

NMR CDCl₃ 7.40-7.10 (9H, m), 3.60 (2H, m) 3.35 (2H, t, J=7.2 Hz) 2.95 (3H, m), 2.50 (2H, t, J=7.2 Hz).

Compound 9, AV 73

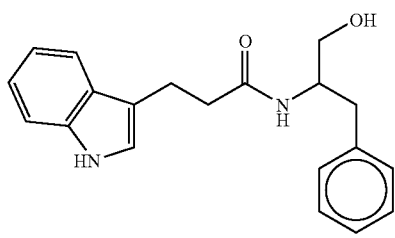

C₂₀H₂₂N₂O₂
Mol. Wt.: 322.40

0.38 g 2 mM, 3-indole propionic acid and 2 ml thionyl chloride in 30 ml cyclohexane were refluxed for 2 hours. Evaporation gave light yellow solid to which were 5 added 0.4 g 2.6 mM, phenyl alaninol in 30 ml dichloromethane and 0.3 ml triethyl amine. After stirring 2.5 hours at room temperature, water and KOH were added to neutral pH and the reaction was extracted with dichloromethane. Evaporation gave 0.47 g pink solid, 75% yield.

NMR CDCl₃ 7.58 (1H, d, J=8.0 Hz), 7.40 (1H, d, J=8.0 Hz), 7.30-6.9 (8H, m), 3.50 (2H, m) 3.30 (2H, t, J=7.5 Hz), 2.95 (3H, m), 2.70 (2H, t, J=7.5 Hz).

Compound 10

0.3 g of Compound 4 (AV 22), 0.8 g triphenyl phosphine and 0.55 g ethyl diazo carboxylate were added to 1 g of poly(propylene glycol), (average molecular weight ca 1000), in 60 ml dichloromethane. Stirring for 2 hours at room temperature, evaporation and chromatography gave 0.65 g of Compound 10, Formula VII, as a viscous oil.

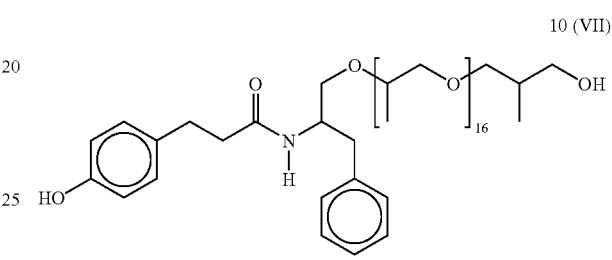

10 (VII)

Additional Compounds Synthesised from Phenyl Alaninol
These compounds include those represented by the following formula:

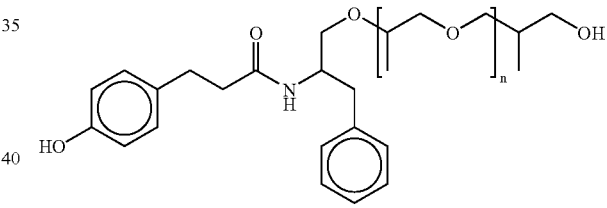

This compound can also be represented as Formula A, where R is a polypropylene glycol polymer and n is the total number of polypropylene monomers in the polymer:

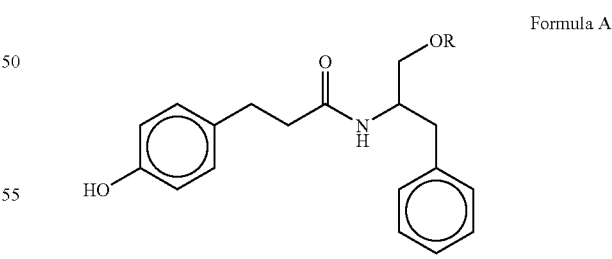

Formula A

AV 61:
R=PPG (polypropylene glycol) n=7 MW-706
0.3 g AV 22 (1 mM), 0.8 g 3 mM, triphenyl phosphine and 0.55 g 3.2 mM, ethyl diazo carboxylate were added to 1 g of poly(propylene glycol) (average mol. weight 424, n=7) in 60 ml dichloromethane. After stirring for 4 hours at room temperature, evaporation and chromatography gave 0.55 g viscous oil, a 73% yield.

NMR CDCl₃ 7.30-6.9 (9H, m), 4.1-3.0 (m), 2.60 (2H, t, J=7.2 Hz), 1.2-1.1 (m)

AV 62
R=PPG n=12 MW-996
Was prepared as above from 0.2 g AV 22 to give 0.3 g 46% yield.

AV 60
R=PPG n=17 MW-1286
Was prepared as above from 0.1 g AV 22 to give 0.2 g 48% yield.

AV 63
R=PPG n=34 MW-2274
Was prepared as above from 0.1 g AV 22 to give 0.25 g 34% yield.

AV 132

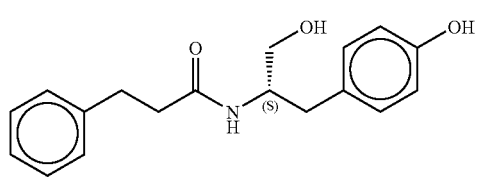

C₁₈H₂₁NO₃
Mol. Wt.: 299.36

Was prepared as the procedure for AV 72, substituting L(−) tyrosinol for the (racemic) tyrosinol to give the above compound, and an undetermined amount of impurity. Use of an adequate protecting scheme to protect the open phenol ring from attack by the propylene glycol should reduce the amount of impurity.

AV 133

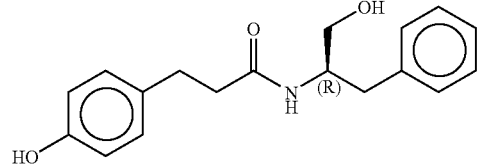

C₁₈H₂₁NO₃
Mol. Wt.: 299.36

Was prepared as the procedure for AV 22, substituting D(+)phenyl alaninol for the (racemic) phenyl alaninol to give the above compound, and an undetermined amount of impurity. Use of an adequate protecting scheme to protect the open phenol ring from attack by the propylene glycol should reduce the amount of impurity.

AV 134

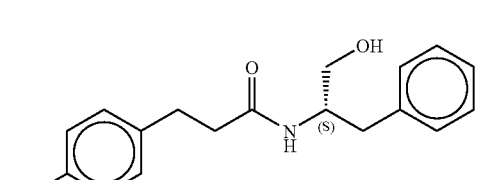

C₁₈H₂₁NO₃
Mol. Wt.: 299.36

Was prepared as the procedure for AV 22, substituting L(+)phenyl alaninol for the (racemic) phenyl alaninol to give the above compound, and an undetermined amount of impurity. Use of an adequate protecting scheme to protect the open phenol ring from attack by the propylene glycol should reduce the amount of impurity.

AV 136

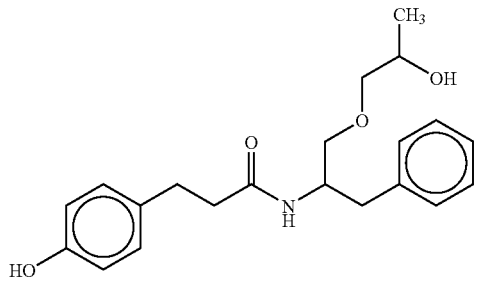

C₂₁H₂₇NO₄
Mol. Wt.: 357.44

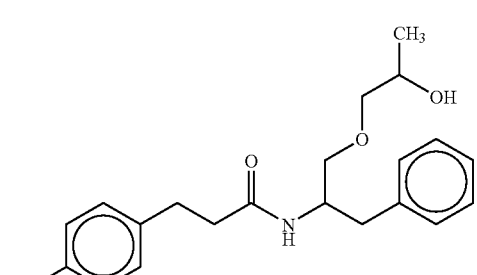

(isomer)

R=PPG n=1
Was prepared as above from AV 22 and from AV 133, to give the compound or its isomer, and an undetermined amount of impurity. Use of an adequate protecting scheme to protect the open phenol ring from attack by the propylene glycol should reduce the amount of impurity.

AV 137

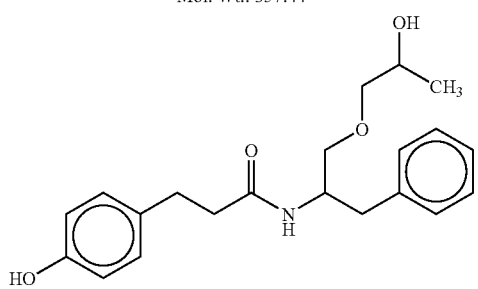

C₂₁H₂₇NO₄
Mol. Wt.: 357.44

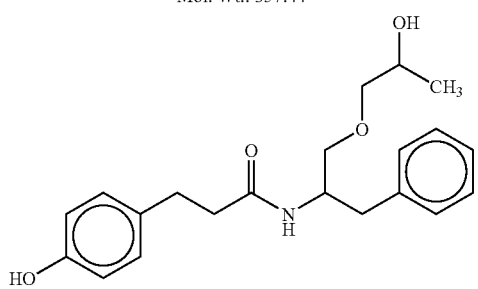

(isomer)

R=PPG n=1

Was prepared as above from AV 22 and from AV 134, to give the compound or its isomer, and an undetermined amount of impurity. Use of an adequate protecting scheme to protect the open phenol ring from attack by the propylene glycol should reduce the amount of impurity.

Compounds Synthesised from Compound 5, AV 57

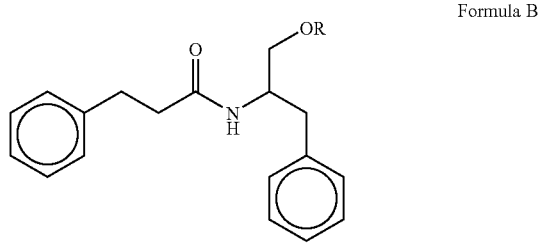

Formula B

AV 86
  R=PPG n=7 MW-690
  Was prepared as above from 0.22 g AV 57 to give 0.25 g, 47% yield.

AV 87
  R=PPG n=17 MW-1270
  Was prepared as above from 0.2 g AV 57 to give 0.33 g, 33% yield.

Compounds Synthesised from Compound 9, AV 73

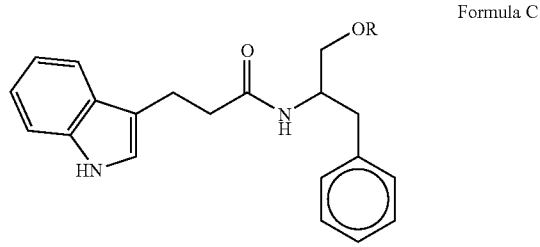

Formula C

AV 76
  R=PPG n=7 MW-729
  Was prepared similar to AV 61 above from 0.22 g AV 73 to give 0.23 g, 47% yield.

AV 77
  R=PPG n=34 MW-2297
  Was prepared as above from 0.2 g AV 73 to give 0.35 g, 25% yield.

Compounds Synthesised from Tyrosinol

Compounds Synthesised from Compound 6, AV 58

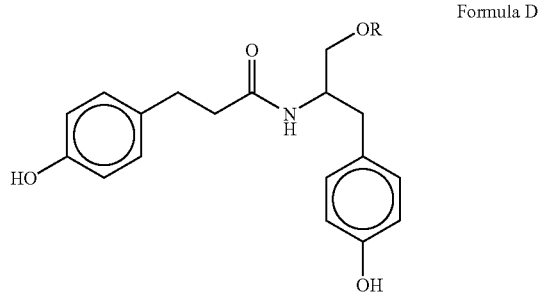

Formula D

AV 64
  R=PPG n=7 MW-722
  Was prepared as above from 0.2 g AV 58 to give 0.21 g, 46% yield.

AV 65
  R=PPG n=17 MW-1302
  Was prepared as above from 0.23 g AV 58 to give 0.28 g, 29% yield.

Compounds Synthesised from Compound 8, AV 72

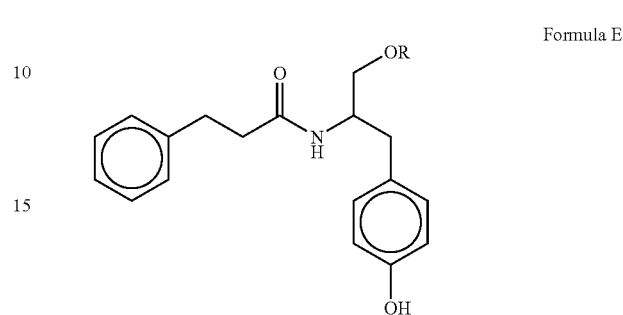

Formula E

AV 74
  R=PPG n=7 MW-706
  Was prepared similar to AV 61, above, from 0.22 g AV 72 to give 0.26 g 50% yield.

AV 75
  R=PPG n=34 MW-2274
  Was prepared as above from 0.2 g AV 72 to give 0.35 gr, 23% yield.

AV 131
  R=PPG n=69 MW-4307
  Was prepared as above from AV 72 and poly(propylene glycol) (average mol. weight 4,000).

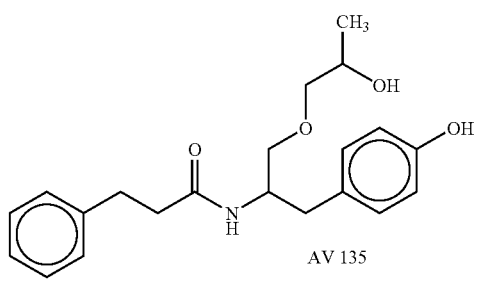

AV 135

$C_{21}H_{27}NO_4$
Mol. Wt.: 357.44

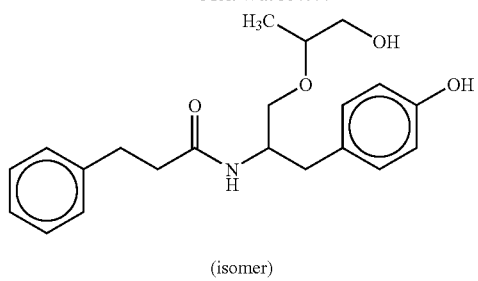

(isomer)

R=PPG n=1
  Was prepared similar to AV 74, above, from AV 72 and from AV 132, to give the compound or its isomer, and an undetermined amount of impurity. Use of an adequate protecting scheme to protect the open phenol ring from attack by the propylene glycol should reduce the amount of impurity.

Compounds Synthesised from Tryptophanol

Compounds Synthesised from Compound 7, AV 59

Formula F

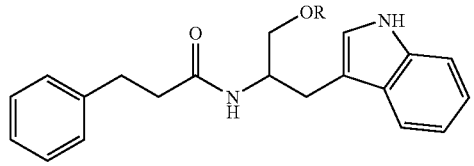

AV 81
R=PPG n=7 MW-729
Was prepared similar to AV 61, above, from 0.22 g AV 59 to give 0.26 g 53% yield.

AV 82
R=PPG n=34 MW-2297
Was prepared as above from 0.2 g AV 59 to give 0.35 g 41% yield.

Example 3

Synthesis of (S) 2-N (3-O-polypropyleneglycol)pro-pylbenzene)-3-(4-hydroxyphenyl)propylamide (AV 61S, n=7)

Reagents and Instrumentation

1-Hydroxybenzotriazole hydrate (HOBt), Aldrich cat. #15, 726-0; N,N'-dicyclohexylcarbodiimide (DCC), Aldrich cat.# D8-000-2; potassium carbonate, Aldrich cat. #46, 781-2; L-phenylalanynol, Fluka cat. #78100; 3-(4-hydroxyphenyl) propionic acid, Fluka cat. #56190; L-tyrosinol hydrochloride, Aldrich, cat. #46, 999-8; hydrocinnamic acid, Aldrich, cat. #13, 523-2; methanesulfonyl chloride, Aldrich cat. #47, 125-9; poly(propylene glycol) $M_n$=425, Aldrich cat. #20, 230-4; poly(propylene glycol) $M_n$=1000, Aldrich cat. #20,232-0. THF and acetonitrile were dried over KOH pellets for at least 48 hours prior to use. methanesulfonyl chloride (mesyl chloride) and pyridine were distilled prior to use. TLC tests were carried out with Merck's $60F_{254}$ silica-gel on aluminium plates. Column chromatographic separations were made with Merck's Kieselgel 60 silica gel. UV lamp (λ254 nm) was used to detect UV absorbing spots on the TLC plates. Proton NMR tests were made on Bruker's Avance 500 and Avance 200 instruments. Mass-spectral analyses of small molecular weight molecules were made on Bruker's Esquire $3000^{plus}$ mass-spectrometer and of the PPG-containing molecules on Bruker's MALDI-TOF (reflex IV) mass-spectrometer. Using a chromatotron is recommended for a better controlled chromatographic separations.

Synthesis of 1 (S Isomer)

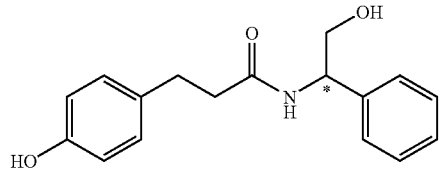

3-(4-Hydroxyphenyl)-propionic acid (0.2 g, 1.2 mmol), L-phenylalaninol (0.18 g, 1.2 mmol), N-hydroxybenzotriazole (HOBt) (0.16 g, 1.2 mmol) and THF (5 mL) were put into a round-bottom flask equipped with a magnetic stirrer. The flask was cooled in an ice-water bath and a pre-cooled solution of dicyclohexylcarbodiimide (DCC) (0.26 g, 1.26 mmol) in 3 mL THF was introduced dropwise into the reaction mixture. The reaction mixture was allowed to stir for additional 1 hour at low temperature and then for another 2 hours at room temperature. The white precipitate formed was filtered out and the filtrate was evaporated to dryness. The residue was dissolved in 10 mL ethyl acetate and the organic phase washed twice with 1M HCl, then twice with a saturated solution of sodium bicarbonate solution and then once with water. The organic phase was dried over anhydrous magnesium sulfate, paper filtered and evaporated to about a quarter of its original volume. The remaining solution was allowed to cool and the crystalline precipitate formed was recovered by vacuum filtration to yield 0.24 g of 1 (67%).

Synthesis of 2 (S Isomer)

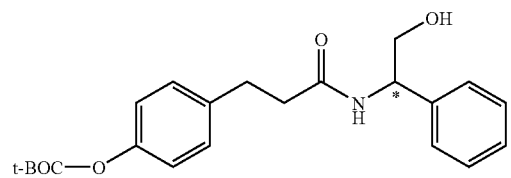

1 (0.1 g, 0.33 mmol), potassium carbonate (0.069 g, 0.5 mmol, thinly crushed) and THF (3 mL, dried over KOH pellets) were put in a round-bottom flask equipped with a magnetic stirrer and a $CaCl_2$ drying tube. The mixture was cooled over an ice-salt bath (−10° C.) and a pre-cooled solution of di-tert-butyldicarbonate (0.066 g, 0.30 mmole) in 2 mL THF (dried) was introduced dropwise. The mixture was allowed to stir at ice temperature for 1 hour and then for 2 days at room temperature. The reaction mixture was then evaporated, water (5 mL) introduced and the product was extracted with two 10 mL portions of ethyl acetate. The combined extracts were dried over anhydrous magnesium sulfate, paper-filtered and the solvent removed. The oily residue was triturated with a small amount of n-hexane and the solid formed recovered by vacuum filtration (Yield 0.12 g, 90.1%). Alternatively, the oily residue can be dissolved in an 1:1 mixture of ethyl acetate and hexane and the product recrystallized.

Synthesis of 3 (S Isomer)

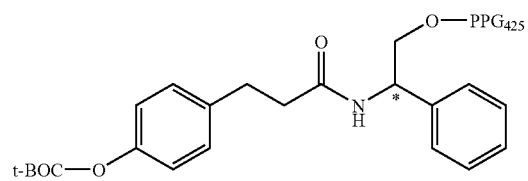

a. Mesylation of PPG.

106 mg of $PPG_{425}$ (0.25 mmol) was reacted with 90 mole-percent of mesyl chloride (26 mg, 2 drops) and 0.4 mmol pyridine (31.6 mg, 2 drops) to afford the mono-mesylated PPG (A). After combining PPG, mesyl chloride and pyridine, the mesylation reaction was carried out at 0° C. during 30 minutes, while stirring, and then continued for another 60 minutes at room temperature. During mixing the reaction mixture turned from colorless to milky-white. The mixture was then dissolved in 5 mL methylene chloride and the organic phase washed twice with 1M HCl solution, then twice with 1M NaOH solution and once with water. The organic phase was dried over anhydrous sodium sulphate, filtered and the solvent removed.

b. Sodium Activation of 2.

0.1 g of 2 (0.25 mmol) was dissolved in 5 mL of absolute ethanol and then reacted with an equi-molar amount of sodium-ethoxide in absolute ethanol (previously prepared by reacting 0.25 mg-atom of sodium with an access of absolute ethanol). The ethanol of the combined solutions was evaporated to total dryness to yield the sodium salt of 2 (B).

c. Reacting A and B

A was dissolved in 5 mL of a potassium hydroxide-dried acetonitrile and the solution introduced into a round-bottom flask containing a magnetic stirrer. 5 mL of dried acetonitrile solution of B was introduced into the flask, followed by a catalytic amount (few crystals) of potassium iodide. A reflux condenser and a gas bubbler adjusted on top of it were connected to the reaction vessel and the reaction mixture was allowed to reflux under nitrogen atmosphere, while stirring, during 24 hrs. The reaction mixture was then paper-filtered and the solvent removed. The residue was dissolved in 2 mL of ethyl acetate and then passed through a silica-gel column, using ethyl acetate for elution. The TLC (elution with ethyl acetate) UV-absorbing spot at $R_f$=0.55 turned out to contain the desired product 3 (a mixture of molecules containing different PPG sub-unit lengths), however, containing also some unreacted PPG. Other fractions contained unreacted mesylated PPG and doubly-mesylated PPG.

Synthesis of 4 (AV 61S)

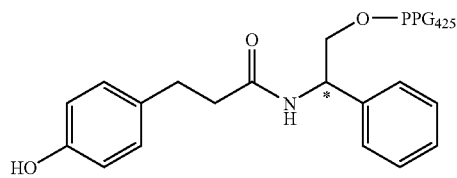

4

40 mg of 3 were dissolved in 3 mL of methylene chloride and 10 drops of tri-fluoroacetic acid (TFA) were added. The mixture was gently heated on a hot plate, while at the same time removing the solvent and TFA by directing a stream of nitrogen gas at the reaction mixture. The remaining is an oil-like product, containing target product 4 (a mixture of molecules containing different lengths of the PPG sub-units and also unreacted PPG chains).

Example 4

Synthesis of (S) 2-N (3-O-(polypropyleneglycol)-1-propyl-4-hydroxybenzene)-3-phenylpropylamide (AV 74S, n=7)

Synthesis of 5 (S Isomer)

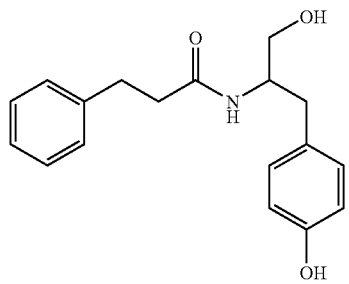

5

Hydrocinnamic acid (36.8 mg, 0.24 mmol), L-tyrosinol hydrochloride (0.05 g, 0.24 mmol), N-hydroxybenzotriazole (HOBt) (0.033 g, 0.24 mmol), sodium bicarbonate (84 mg, 1 mmol) and THF (5 mL) were put into a round-bottom flask equipped with a magnetic stirrer. The flask was cooled in an ice-water bath and a pre-cooled solution of dicyclohexylcarbodiimide (DCC) (53 mg, 0.26 mmol) in 3 mL THF was introduced dropwise into the reaction mixture. The reaction mixture was allowed to stir for another 1 hour at low temperature and then 2 hours at room temperature. The white precipitate formed was paper-filtered and the filtrate evaporated to dryness. The residue was dissolved in 10 mL ethyl acetate. (Some precipitate that may occur at this stage must be filtered out). The clear organic filtrate was twice washed with 1M HCl, then twice with a saturated aqueous solution of sodium bicarbonate and then once with water. The organic phase was dried over anhydrous magnesium sulfate and paper filtered. TLC showed three UV-absorbing spots (eluant ethyl acetate), one at $R_f$=0.55, the second at $R_f$=0.35 and the third at $R_f$=0.05. Proton NMR (methyl sulfoxide) indicated that the spot at $R_f$=0.35 is of compound 5. This component was separated on a silica-gel column (elution with ethyl acetate), yielding 25 mg of 5 (yield: 35%). Alternatively, a quite pure compound 5 (yield 85%) can be obtained by recrystallysing the reaction mixture from methylene chloride.

Synthesis of 6 (S Isomer)

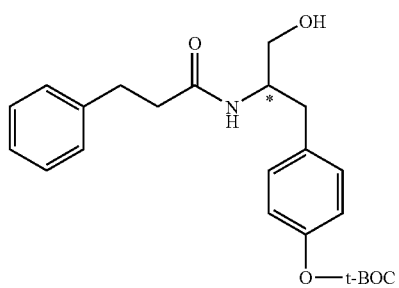

6

Same as synthesis of compound 2. (Yield: 73%).

Synthesis of 7 (S Isomer)

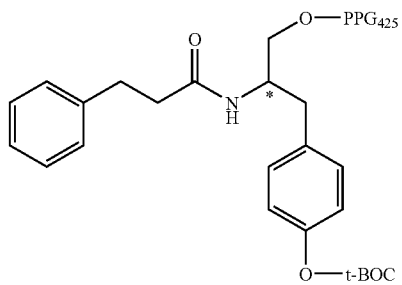

7

Same as synthesis of compound 3. The reaction mixture was chromatographed on a silica-gel column (eluant: ethyl acetate) and a fraction containing UV-absorbing spot ($R_f$=0.43, eluant ethyl acetate) proved by MALDI-TOF mass-spectrometer to contain 7 (a mixture of molecules containing PPG chains of different size), along with unreacted PPG chains and some unreacted mesylated PPG chains.

Synthesis of 8 (AV 74S)

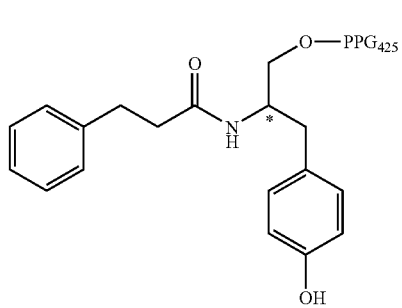

8

Same as synthesis of compound 4.

Analogues of compounds 4 (AV 61S) and 8 (AV 74S) containing $PPG_{1000}$ chains (n=17) (AV 60 S and AV 78S, respectively) were prepared using the same synthetic route as given for the $PPG_{425}$-Containing counterparts.

TLC data of the PPG$_{1000}$ analogues:
PPG$_{1000}$ analogue of AV61S (AV60S): spot at R$_f$=0.40 (eluant: ethyl acetate).
PPG$_{1000}$ analogue of AV74S (AV78S): spot at R$_f$=0.43 (eluant: ethyl acetate).

Example 5

Effect of AV Compounds on Inhibiting CXCR4 and CXCR3

Shearflow experiments. Soluble, affinity purified seven-domain human VCAM-1, sVCAM-1 together with the chemokine SDF-1 (ligand for CXCR4) or Mig (Ligand for CXCR3) were mixed in coating media (PBS buffered with 20 mM sodium bicarbonate pH8.5) and adsorbed as 10 μl drops on a polystyrene plate (60×15 mm Petri dish, Becton Dickinson, Lincoln Park N.J.) over night at 4° C. The plate was then washed and blocked with human serum albumin, HSA (20 mg/ml PBS) for 2 hr at 4° C. To co-immobilize SDF-1 and Mig with the adhesive substrates, the ligands (VCAM-1) were coated in the presence of active (2 μg/ml) or heat denatured SDF-1 or Mig and HSA (2 mg/ml) and washed and quenched as above. A polystyrene plate with coated adhesive substrates was assembled as the lower wall in a parallel plate flow chamber (260 μm gap) mounted on the stage of an inverted phase contrast microscope (Diaphot 300, Nikon) and extensively washed with binding medium. All experiments were conducted at 37° C. Treated (1 hr incubation with 0.1, 1, 10 μg/ml of AV 61, 63, 75, 77) and untreated T cells were diluted with binding medium and perfused into the chamber at 10$^6$ cells/ml by an automated syringe pump (Harvard Apparatus, Natick, Mass.). All experiments were recorded on videotape by a long integration camera LIS-700 CCD (Applitech, Holon Israel) and a SVHS time lapse video recorder (AG-6730 Panasonic). The human T cells were allowed to accumulate for 1 min on the substrate and then the flow rate was increased to 22 dyn/cm$^2$. All recorded images of cells interacting with the adhesive substrates were analyzed and quantified by computer tracking individual cells. The results obtained for each experiment were normalized according to the total number of videotaped cells.

As can be seen from the results of the experiments, shown in FIGS. 1A-1C (CXCR4) and FIGS. 2A-2D (CXCR3), compounds of the invention are effective in inhibiting these cytokine receptors, and as such should be useful in treating HIV and AIDS via preventing the function of this receptor, which is the most important receptor for the entrance of the HIV-1 T tropic into its target cell.

Example 6

Effect of AV Compounds on AICD

T cells were isolated from buffy coats (BC) of consenting normal human donors (Hadassah Hospital Blood Bank). The BC preparations were diluted 1:4 with phosphate-buffered saline (PBS) that contained 10 U/mL heparin. Peripheral blood mononuclear cells were separated by Ficoll/Paque density centrifugation. Monocytes and B cells were depleted by plastic adherence and passage through nylon wool columns, respectively. Small T lymphocytes were harvested from the pellet of a discontinuous Percoll gradient. The cells were found to be >80% CD3+ by FACS analysis. Cells were cultured in the presence of various concentrations of compound and/or phytohemaglutinin (PHA) (1 μg/ml) T cell mitogen. Proliferation was measured by culturing 1×10$^5$ cells in each well of a 96-well flat-bottomed microtiter plates. 48 hrs and 7 days following addition of compound, 1 μCi $^3$[H] thymidine was added to each well and the cultures were incubated for an additional 24 hrs. Samples were harvested and incorporated radioactivity was measured. A 7 day incubation with compounds led to a significant increase in the proliferation of PHA-stimulated T cells versus PHA alone.

Figure 3:
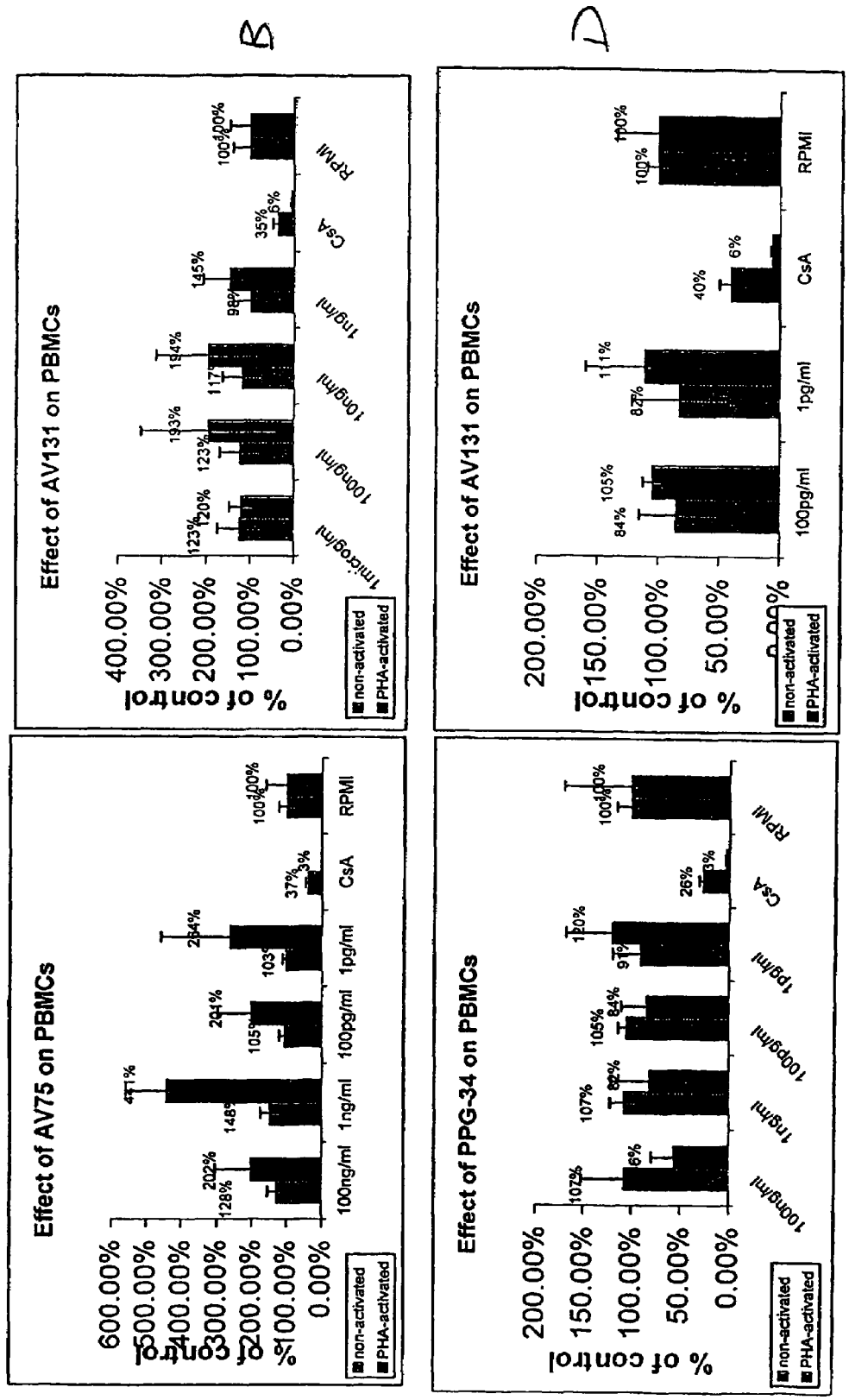
Figure 4:
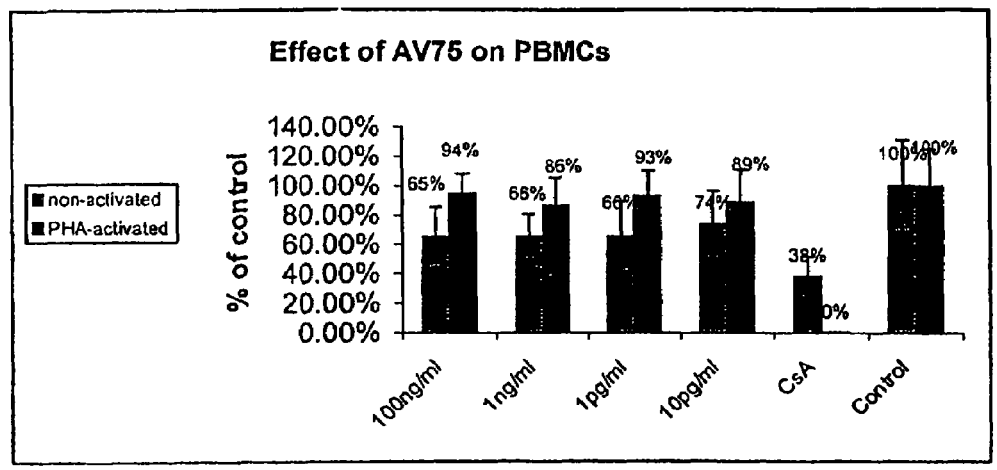
Figure 4:
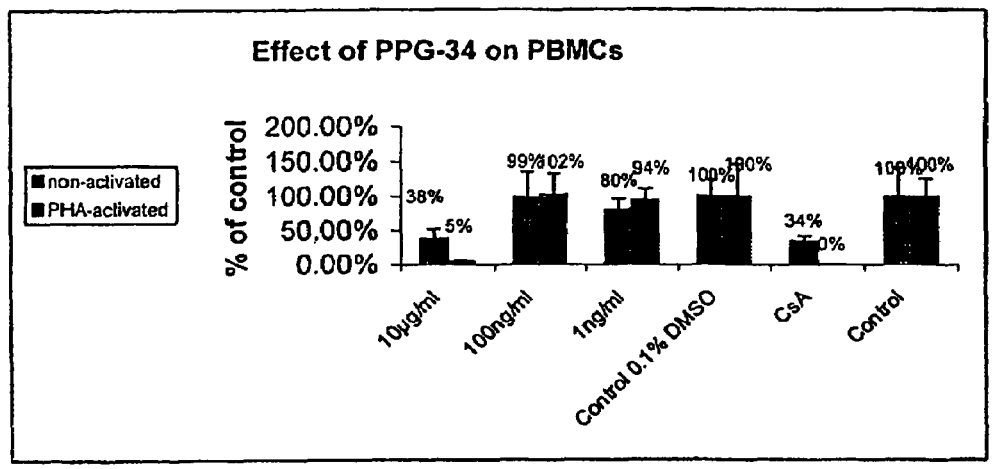
Figure 4:
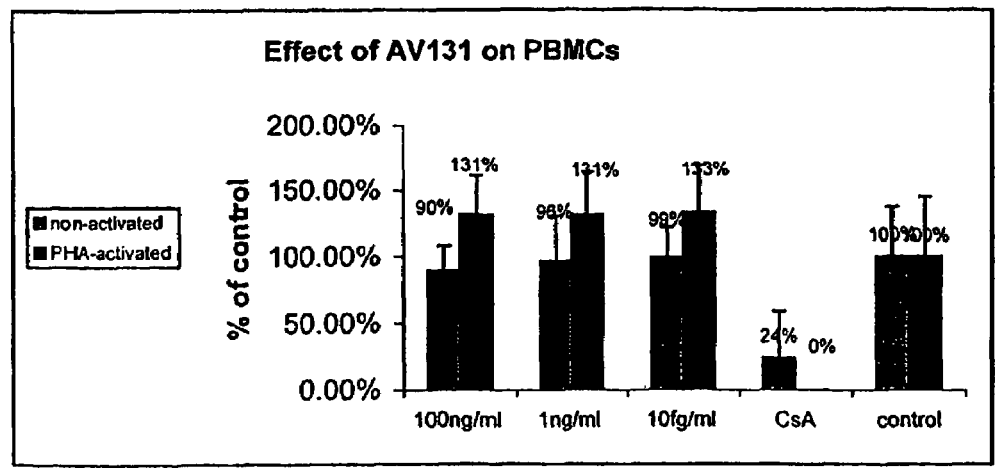
Figure 5:
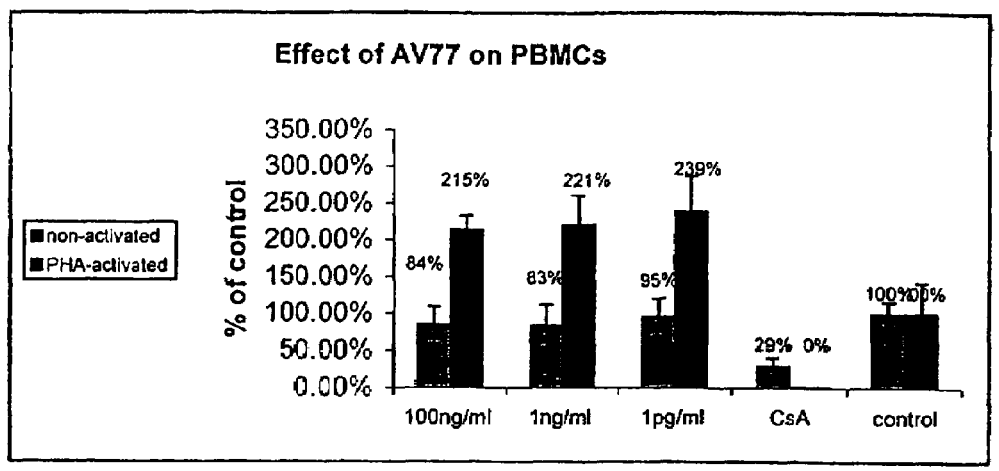
Figure 5:
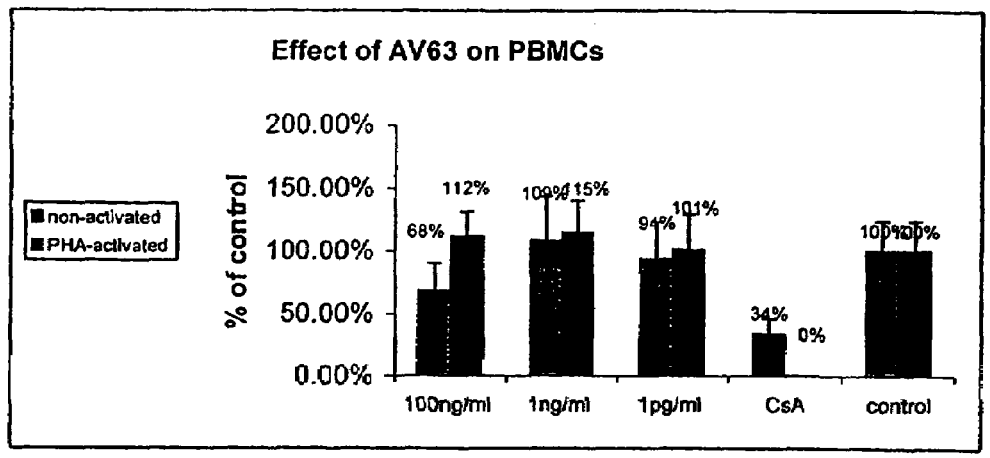
Figure 6:
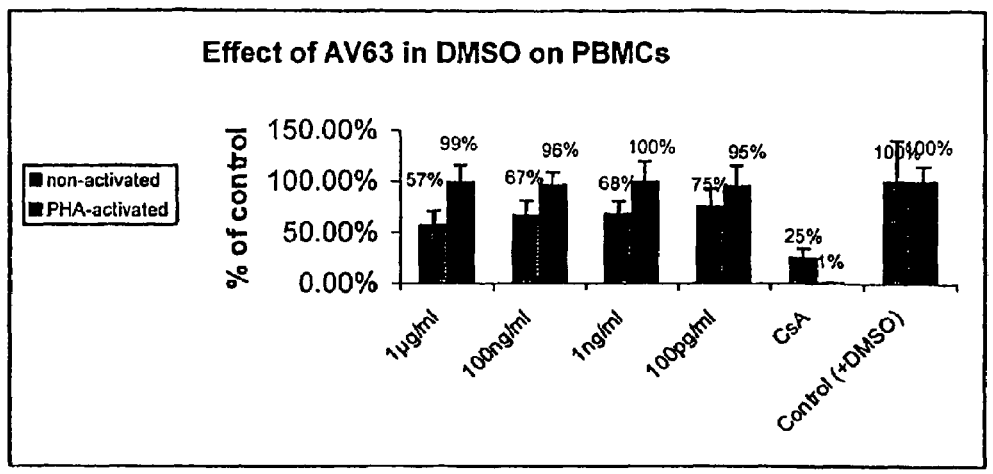
Figure 6:
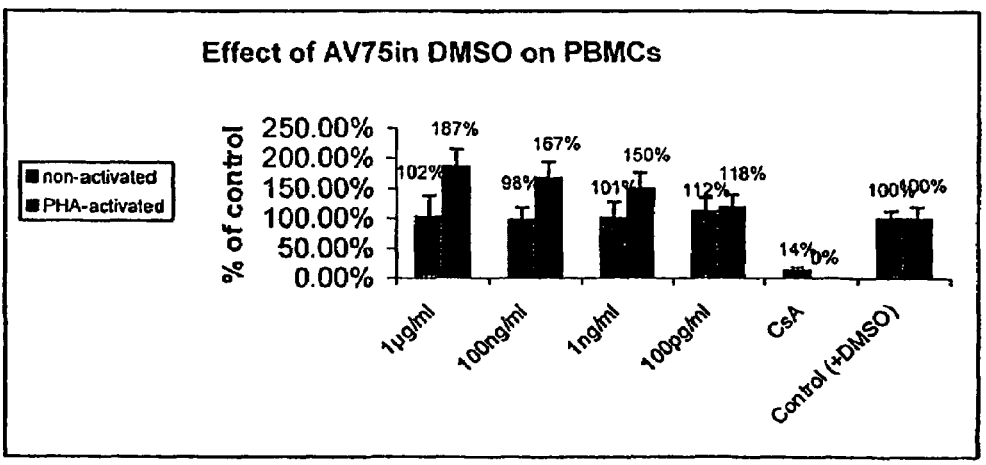
Figure 6:
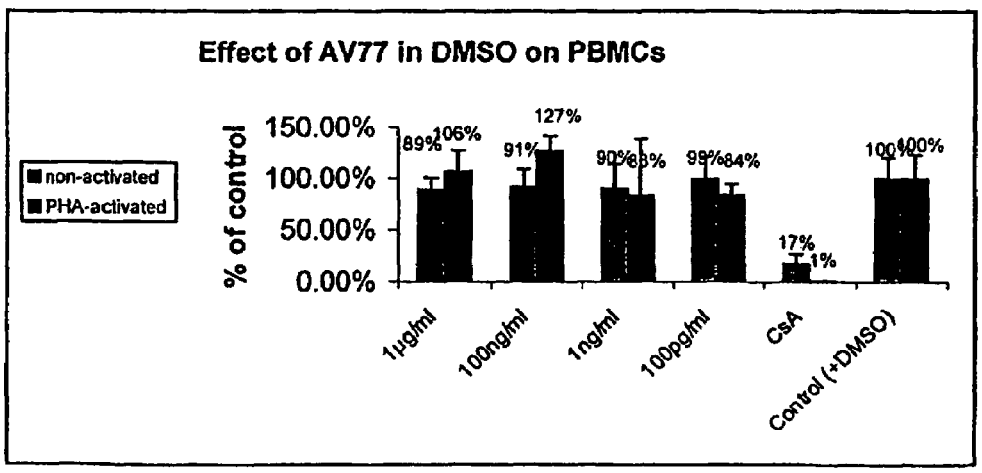
Figure 7:
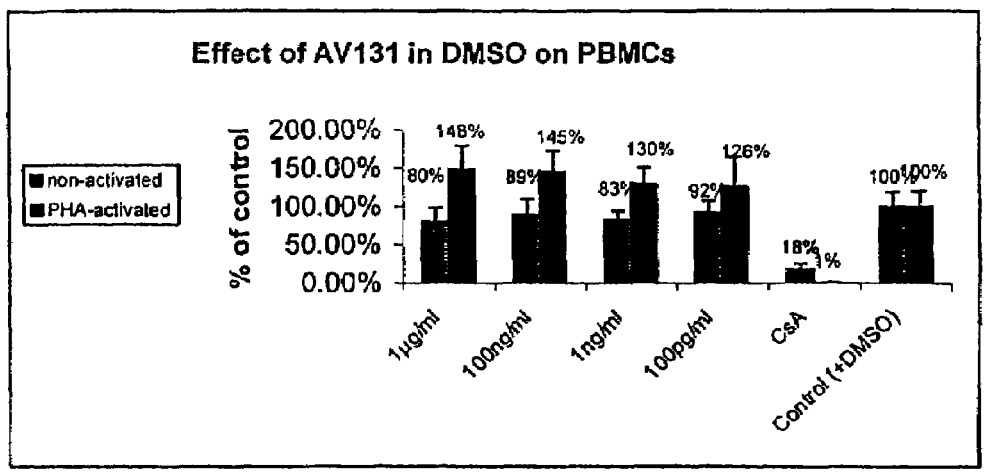

The effect of AV 63, AV 75, AV 77, AV 131, and polypropylene glycol ("PPG-34", MW 2000, as a control) on PHA (phytohemagglutinin)-treated human peripheral blood mononuclear cells (PMBCs), using DMSO as a carrier, was investigated. Data from the AV 63 experiment is shown in FIGS. 5B and 6A. Data from the AV 75 experiment is shown in FIGS. 3A, 4A and 6B. Data from the AV 77 experiment is shown in FIGS. 5A and 6C. Data from the PPG-34 experiment is shown in FIGS. 3C and 4B. Data from the AV 131 experiment is shown in FIGS. 3B, 3D, 4C and 7A. Data from the AV 77 experiment is shown in FIGS. 5A and 6C.

As can be seen from the results of the experiments, shown in the above-mentioned figures, compounds of the invention surprisingly show the enhanced lymphocyte proliferation and apoptotic effect which is characteristic of activation-induced cell death (AICD.)

Example 7

Effect of AV Compounds on Inhibiting Fibrosis

The effect of AV compounds on fibroblast proliferation was investigated. A thymidine (TdR) incorporation experiment was conducted to determine the effect of combined AV molecules on human foreskin fibroblast cells (HFF).

Method: Quantitation of [3H]thymidine (TdR) incorporation
Control: Cell culture medium
Inhibitor: >50% decrease of cpm relative to control (drug Doxorubicin)

Procedure:
HFF are cultured in DMEM medium +1% Na-Pyruvate, 1% Pen/Srep, 1% L-Glu, 1% none-essential amino acid and 10% FBS. The cells were plated at 5×10$^3$/well in a 96 well plate. Extracts were added one day after seeding cells. The cells were incubated for 4 days. 2 days before the end of the experiment, [3H]-thymidine (1 mCi/well) was added. TdR-1:50 (20 ml in 1 ml) (NET-027 Thymidine [methyl-3H] from NEN 6.7 Ci/mmol Batch 3106446) Cells were harvested by adding denaturated agent and scintillation liquid and then counted for 1 min/sample.

Compounds used (AV 61, AV 63 AV 74, AV 75, AV 76, AV 77, AV 81, and AV 82) were resuspended in medium, and diluted to the concentrations indicated in the Figures. Controls were: 1) negative-medium 2) Positive-10^-5M Doxorubicin.

Figure 8:
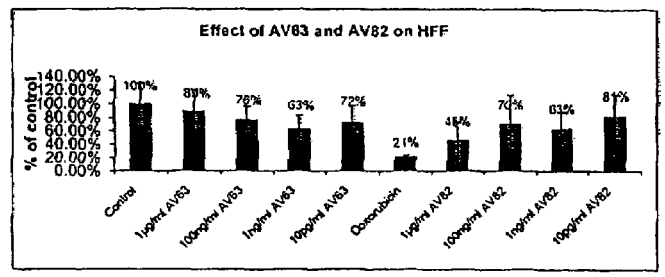
Figure 8:
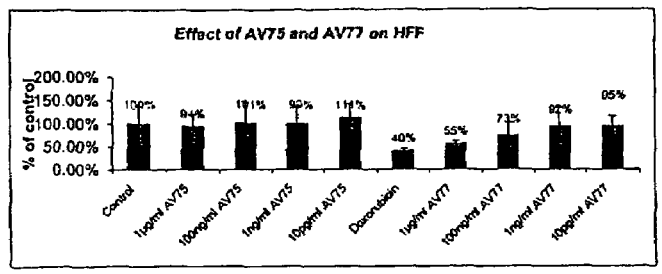
Figure 8:
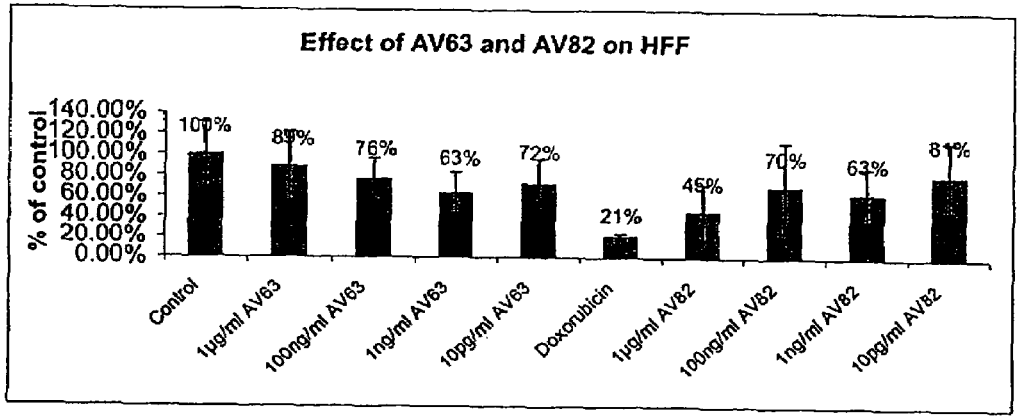
Figure 8:
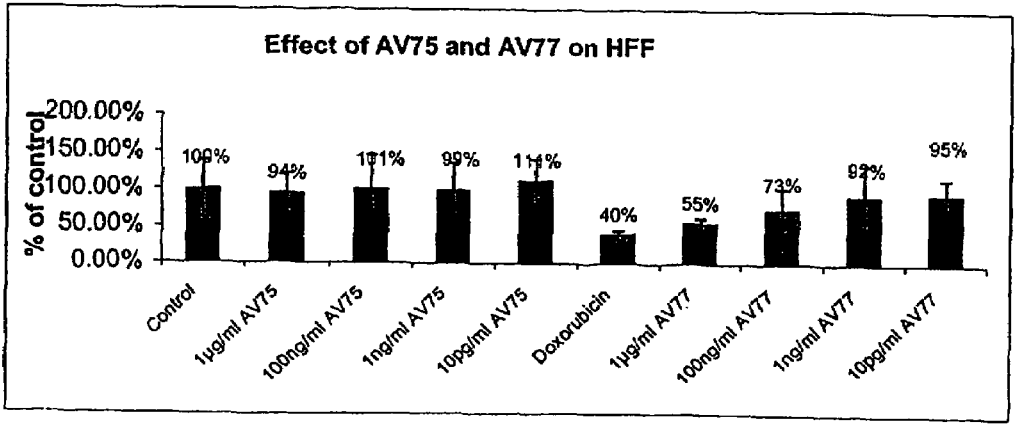
Figure 9:
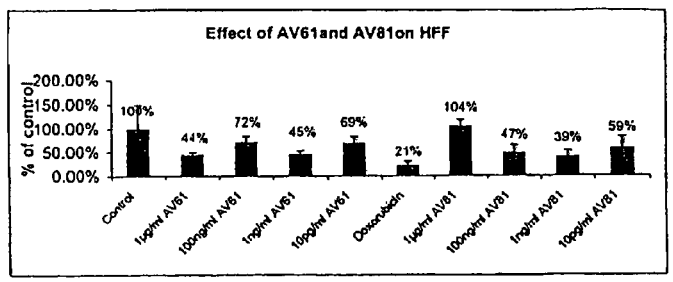
Figure 9:
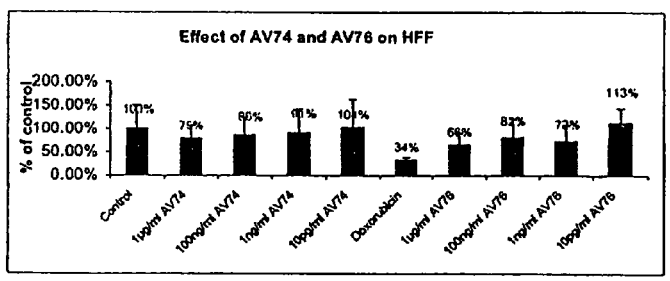
Figure 9:
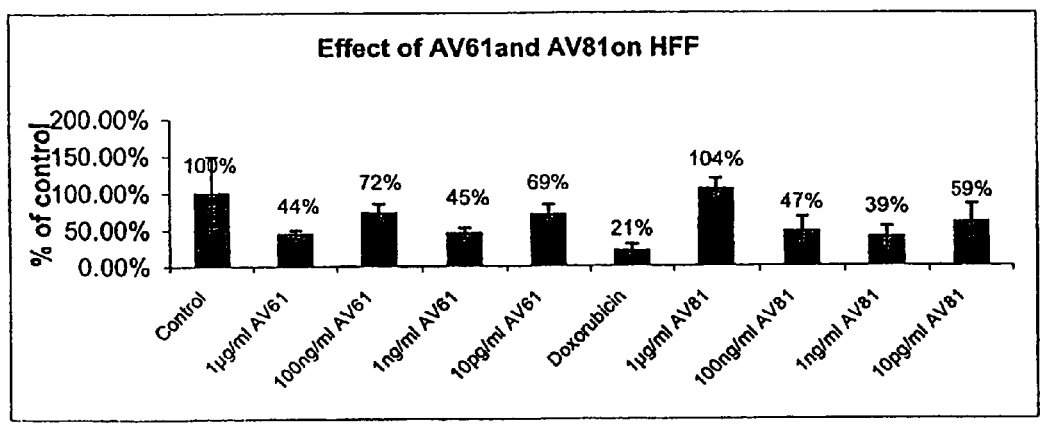
Figure 9:
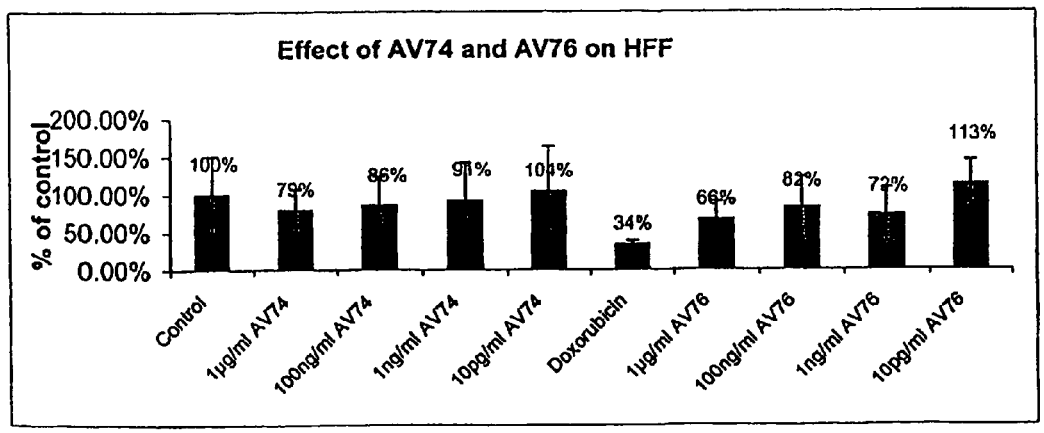

Data from the experiments are shown in FIGS. 8 and 9. As can be seen from the results of the experiments, compounds of the invention are effective inhibitors of fibroblast proliferation.

Example 8

AV Compound Selectivity Index

Anti-HIV-1 results obtained with AV 61 show activity against HIV-1 (III$_B$ strain) with an EC$_{50}$ and CC$_{50}$ of as low as 15.6 μg/ml and 125 μg/ml, of pure substance, resulting in a selectivity index of greater than 8, and a % PR of as high as 100%, as was determined by an MTT-assay.

The following experimental procedures were employed. MT-4 cells were grown in RPMI 1640 medium (Life Technologies, Merelbeke, Belgium), supplemented with 10% (v/v) heat-inactivated fetal calf scrum (FCS), 2 mM L-glutamine, 0.1% sodium bicarbonate and 20 μg/ml gentamicin (Life Technologies, Merelbeke, Belgium). The cells were maintained at 37° C. in a humidified atmosphere of 5% $CO_2$ in air. Every 3-4 days, cells were seeded at $3 \times 10^5$ cells/ml.

Stocks of HIV-1 $III_B$ strain were obtained from the culture supernatant of $4 \times 10^5$ MT4 cells/ml infected with HIV at 400 $CCID_{50}$ immediately after complete cytopathic effect (CPE) has appeared. The virus titre of the supernatant was determined in MT-4 cells using the Reed and Muench end-point dilution method. The virus stocks were aliquoted and stored at −70° C. until used.

Flat-bottom, 96-well plastic microtiter trays (Nunc, Roskilde, Denmark) were filled with 100 ml of complete medium using a Titertek Multidrop dispenser (ICN Biomedicals-Flow Laboratories). Stock solution (10× final test concentration) of AV 61, were added in 25 µl volumes to two series of triplicate wells to allow simultaneous evaluations of their effects on HIV- and mock-infected cells. Serial five-fold dilutions were made directly in the microtiter trays using a Biomek 2000 robot (Beckman, Fullerton, Calif.). Untreated control and mock-infected cell samples were included. 50 µl of HIV at 100 $CCID_{50}$ or medium was added to either HIV-infected or mock-infected part of a microtiter tray. Exponentially growing MT-4 cells were centrifuged for 5 min at 140×g, and the supernatants were discarded. The MT-4 cells were resuspended at $6 \times 10^5$ cells/ml in a flask connected with an autoclavable dispensing cassette of a Titertek Multidrop dispenser. Under slight magnetic stirring, 50 µl volumes were then transferred to the microtiter tray wells. The outer row wells were filled with 200 µl of medium. The cell cultures were incubated at 37° C. in a humidified atmosphere of 5% $CO_2$ in air. The cells remained in contact with the test compounds during the whole incubation period. Five days after infection, the viability of mock and HIV-infected cells was examined spectrophotometrically by the MTT method as described hereinbelow.

The MTT assay is based on the reduction of the yellow coloured 3-(4,5-dimethylthiazol-2-yl)-2,5-diphenyltetrazolium bromide (MTT) (Sigma Chemical Co., St. Louis, Mo.) by mitochondrial dehydrogenase of metabolically active cells to a blue formazan which can be measured spectrophotometrically.

To each microtiter well, 20 µl of a solution of MTT (7.5 mg/ml) in phosphate-buffered saline was added using the Titertek Multidrop. The trays were further incubated at 37° C. in a 5% $CO_2$ incubator for 1 hr. A fixed volume of medium (150 µl) was then removed from each cup using the Biomek 2000 robot without disturbing the MT-4 cell clusters containing the formazan crystals. Solubilization of the formazan crystals was achieved by adding 100 µl of 10% (v/v) Triton X-100 in acidified isopropanol (2 ml concentrated HCl per 500 ml solvent) using the Biomek 2000 robot. Complete dissolution of the formazan crystals could be obtained after the trays had been placed on a plate shaker for 10 min (ICN Biomedicals Flow Laboratories). Finally, the absorbances were read in an eight-channel computer controlled Titertek Microplate reader and stacker (Multiskan MCC, ICN Biomedicals-Flow Laboratories) at two wavelengths (540 and 690 nm). The absorbance measured at 690 nm was automatically subtracted from the absorbance at 540 nm, to eliminate the effects of non-specific absorption. Blanking was carried out directly on the microtiter trays with the first column wells which contained all reagents except MT-4 cells, virus and compounds. All data represent the average values for a minimum of three wells. The 50% cytotoxic concentration ($CC_{50}$) was defined as the concentration of compound that reduced the absorbance ($OD_{540}$) of the mock-infected control sample by 50%. The percent protection achieved by the compounds in HIV-infected cells was calculated by the following formula:

$$\frac{(OD_T)HIV - (OD_C)HIV}{(OD_C)\text{mock} - (OD_C)HIV} \quad \text{expressed in \%}$$

wherein $(OD_T)HIV$ is the optical density measured with a given concentration of the test compound in HIV-infected cells; $(OD_C)HIV$ is the optical density measured for the control untreated HIV-infected cells; $(OD_C)$ mock is the optical density measured for the control untreated mock-infected cells; and all O.D. values were determined at 540 nm. The concentration achieving 50% protection according to the above formula was defined as the 50% effective concentration ($EC_{50}$).

The results showed that AV 61 has activity against HIV-1 ($III_B$ strain) with an $EC_{50}$ and $CC_{50}$ of as low as 15.6 µg/ml and 125 µg/ml, of pure substance, resulting in a selectivity index of greater than 8, and a % PR of as high as 100%, as was determined by an MTT-assay.

Example 9

Effect of AV 61S and PPG7 on PHA-Activated PBMCs

Figure 10:
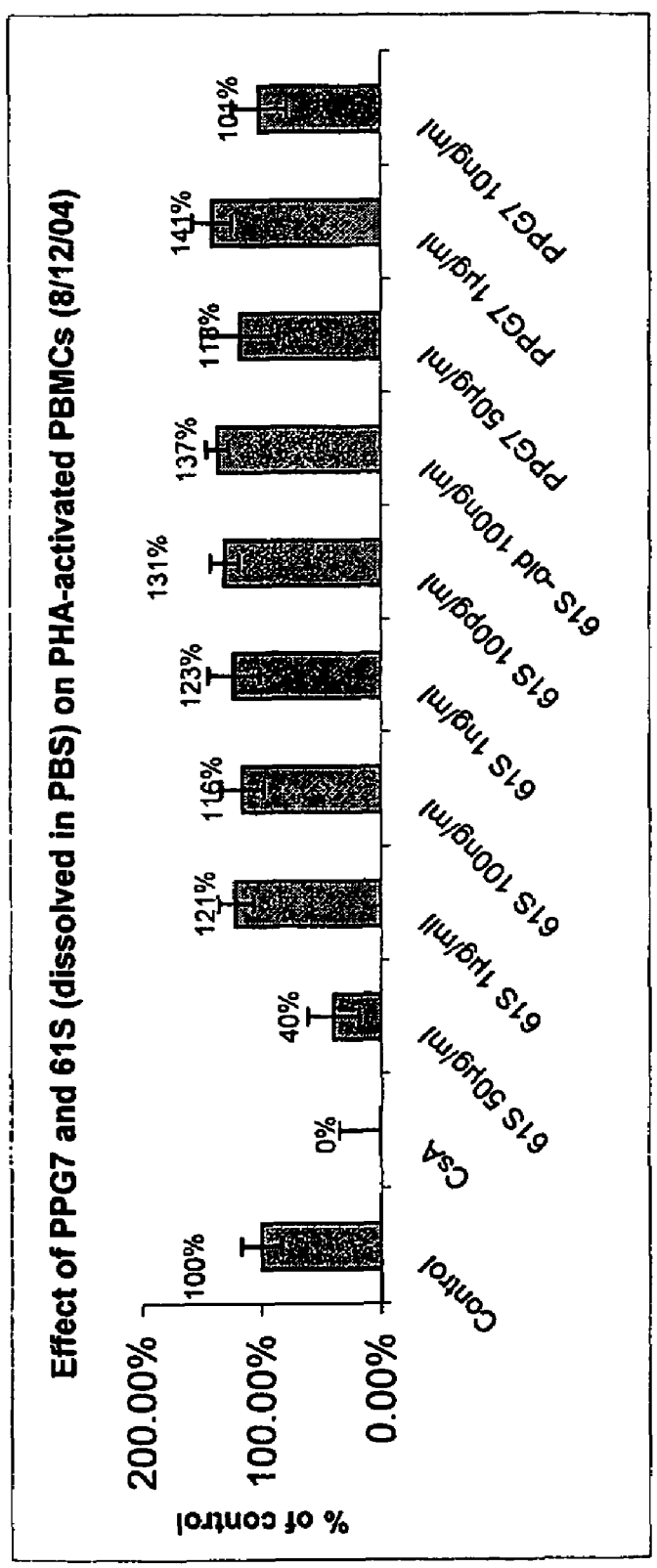

FIG. 10 shows the results of an experiment to investigate the inhibitory effect of AV 61S on PHA-activated PBMCs. Human PBMCs were prepared from a blood bank and plated out at a concentration of $10^5$ cells per well in a standard 96-well plate. PHA was added to each well at a concentration of 10 µg/ml together with AV 61S or PPG-7 (both in PBS) at concentrations of 50 µg/ml, 1 µg/ml, 100 ng/ml, 1 ng/ml and 100 pg/ml respectively for AV 61S and 50 µg/ml, 1 µg/ml and 10 ng/ml for PPG-7. The cells were then incubated for 7 days. [3H]-thymidine (NET-027 Thymidine [methyl-3H] from NEN 6.7 Ci/mmol Batch 3106446) was added to each well 48 hours after plating at a concentration of 1 mCi/well; a second dose was added to each well 18 hours before the end of the experiment. The cells were then harvested and counted for 1 min./sample.

The controls were medium alone and CsA (1 mg in 1 ml ethanol).

As can be seen in FIG. 10, 60% inhibition relative to the controls was shown at a concentration of AV 61S of 50 µg/ml.

Example 10

Effect of AV 61S, AV 61 R, AV 74S and AV 74 R on PHA-Activated PBMCs

Example 9 was repeated using separately compounds AV 61S, AV 61R and AV 74S and AV 74R. In each case the test compound was diluted in DMSO to a final concentration of 0.25%. A single dose of [3H]-thymidine (NET-027 Thymidine [methyl-3H] from NEN 6.7 Ci/mmol Batch 3106446) was added to each well 18 hours before the end of the experiment.

Figure 11A:
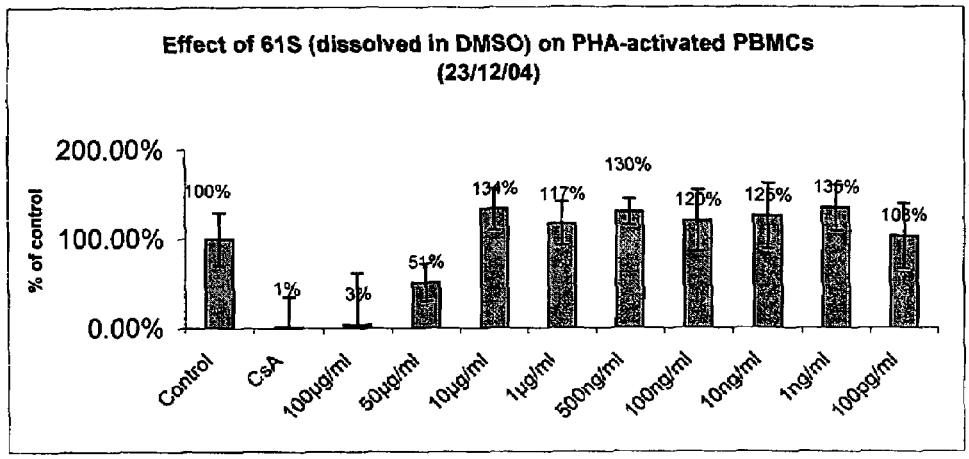
Figure 11B:
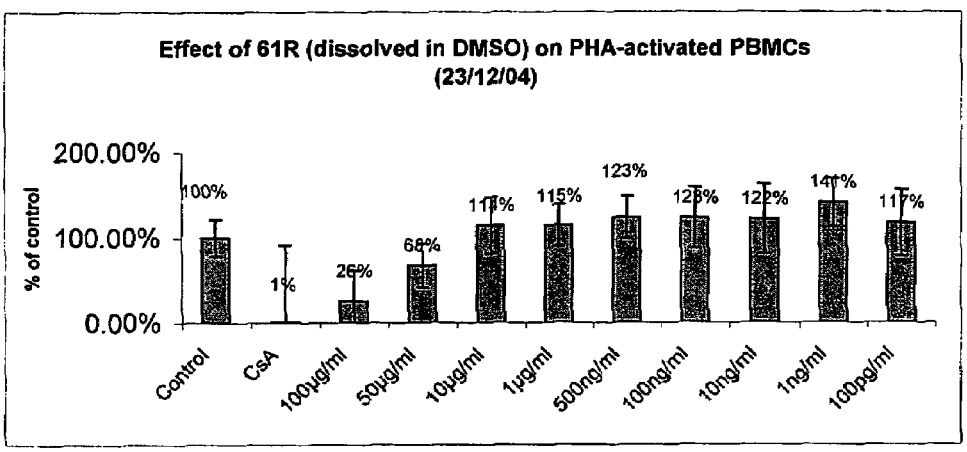
Figure 12A:
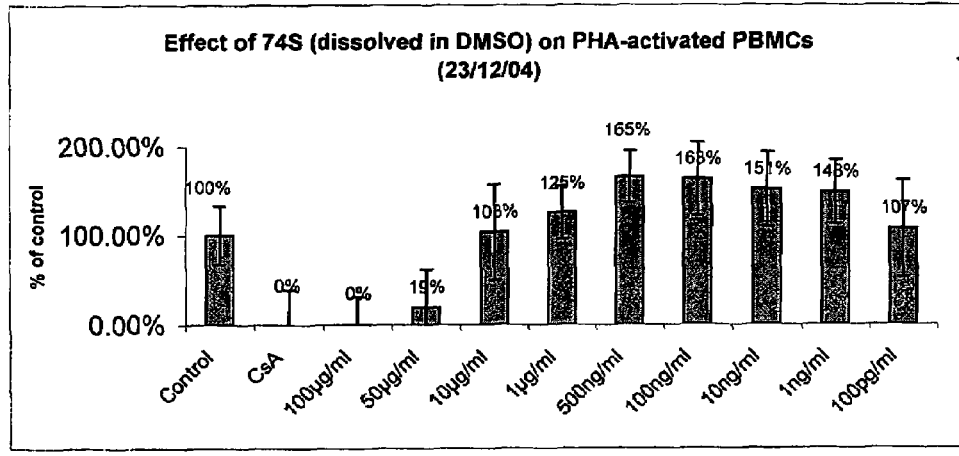
Figure 12B:
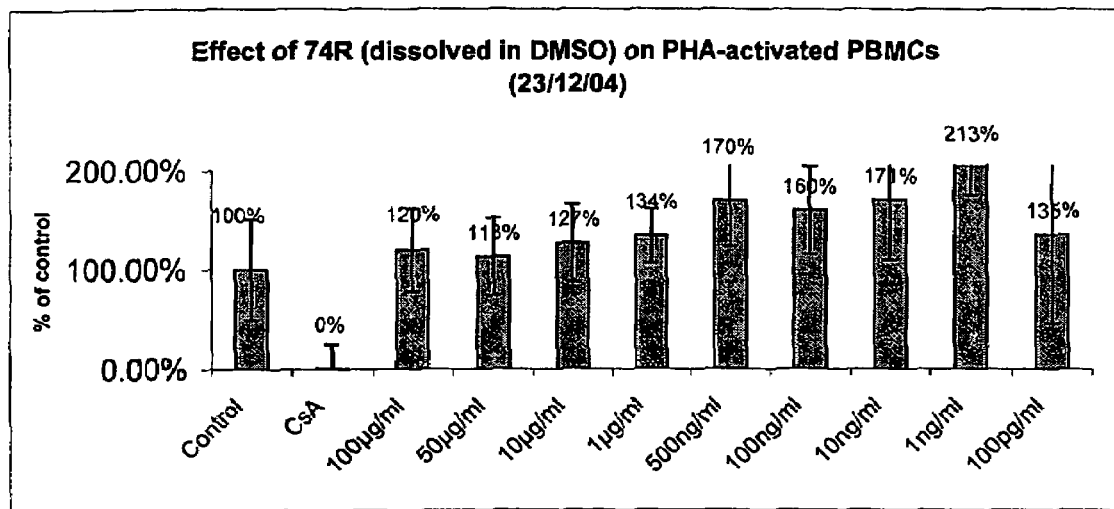

FIGS. 11A and 11B show the results for AV 61S and AV 61R and FIGS. 12A and 12B show the corresponding results for AV 74S and AV 74R. As may be seen, AV 61S shows an inhibitory effect of about 97% relative to the controls at a concentration of 100 µg/ml and about 49% at 50 µg/ml. AV 61R shows a significantly reduced activity, namely 74% inhibition at 100 µg/ml and 42% at 50 µg/ml.

The results for AV 74S and AV 74R show an even more marked difference between the S and R enantiomers of the compound. As may be seen from FIG. 12 A, at 100 µg/ml AV 74S shows 100% inhibition relation to the controls and 81% at 50 μg/ml. AV 74R, as shown in FIG. 12B, shows no inhibition of activated PBMCs. at 100 μg/ml or less.

Example 11

Toxicity of AV Compounds Against PBMC Cells by Alamar Blue Reagent

It has been established in Examples 9 and 10 above that the molecules AV 61S and AV 74S have an inhibitory effect on PBMCs (AV 74R had no effect whereas AV 61R had only a marginal effect) when tested in the concentrations of 100 μg/ml and 50 μg/ml (61S) and 100 ug/ml; 50 μg/ml and 25 μg/ml (74S). A preliminary experiment with Alamar Blue showed that the inhibitory effect was due to an anti-proliferative activity of the molecules rather than to a "killing" effect. In order to check this in more detail, the present experiment was performed:

Human PBMC cells were obtained from a blood bank and plated out on a standard 96-well plate at a concentration of $10^5$ cells/well. PHA (10 μg/ml) and AV 61S (or AV 74S) at different dilutions in DMSO of 100 μg/ml, 50 μg/ml, 25 μg/ml, 10 μg/ml and 1 μg/ml were added simultaneously to each well. The cells were incubated for 24 hours.

After 24 hours, Alamar Blue reagent was added up to 10% of the total well volume.

The controls were medium only and CsA (1 mg/1 ml EtOH).

Figures 13A, 13B:
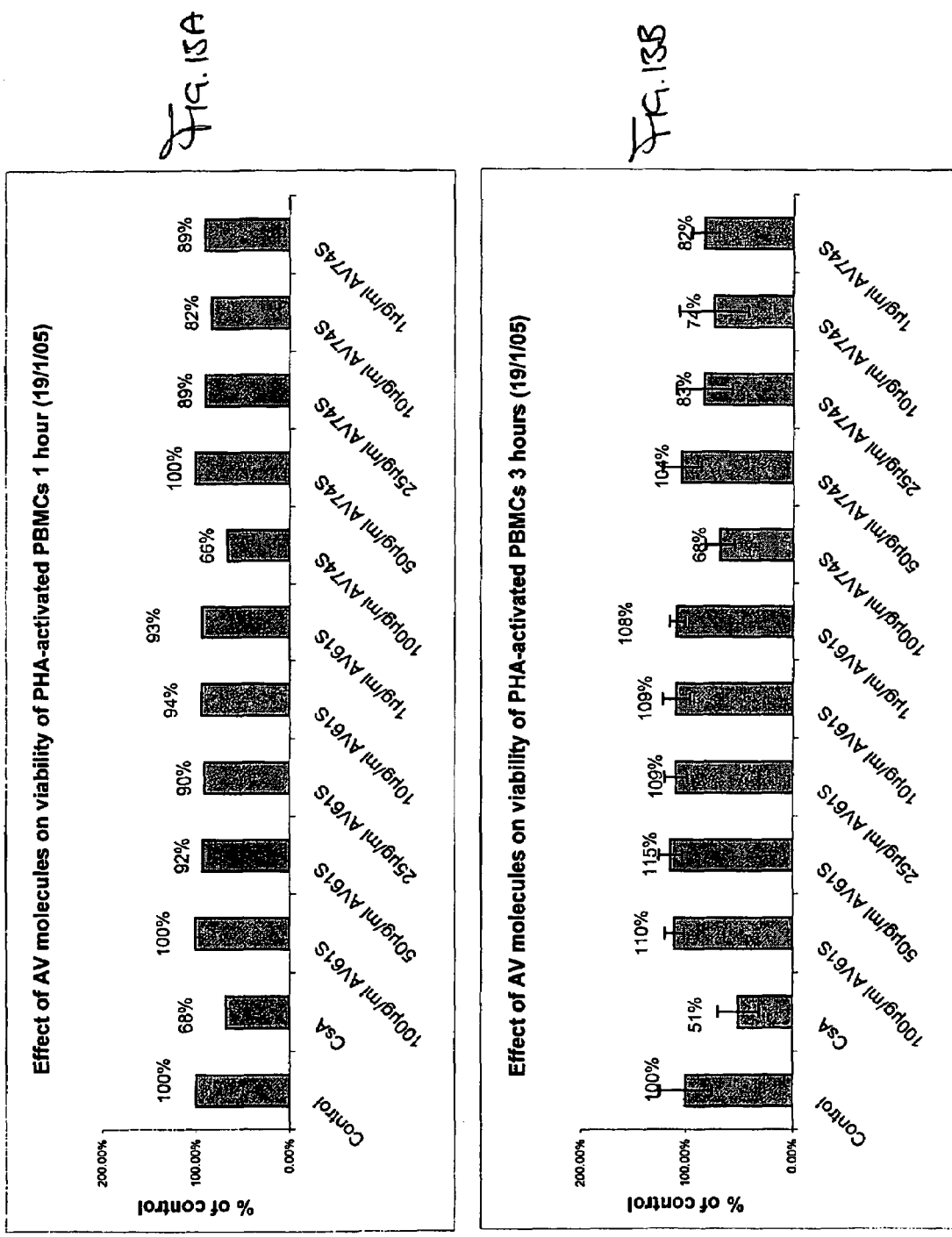
Figure 13C:
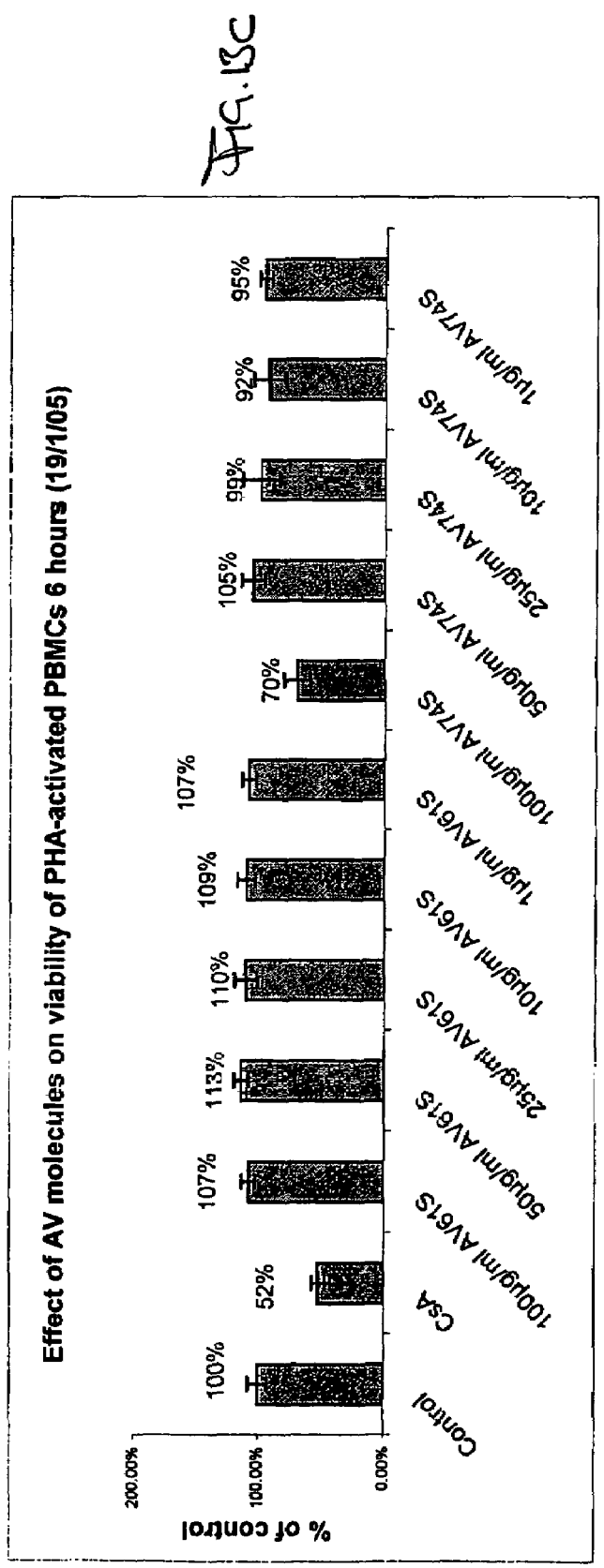

The contents of each well were then assayed 1 hour, 3 hours and 6 hours after addition of Alamar Blue by fluorescence in the manner known to those skilled in the art to determine the viability of the PBMCs. The results are shown in FIGS. 13A-13C.

Example 12

Toxicity of AV Compounds Against PBMC Cells by Alamar Blue Reagent

Figure 14C:
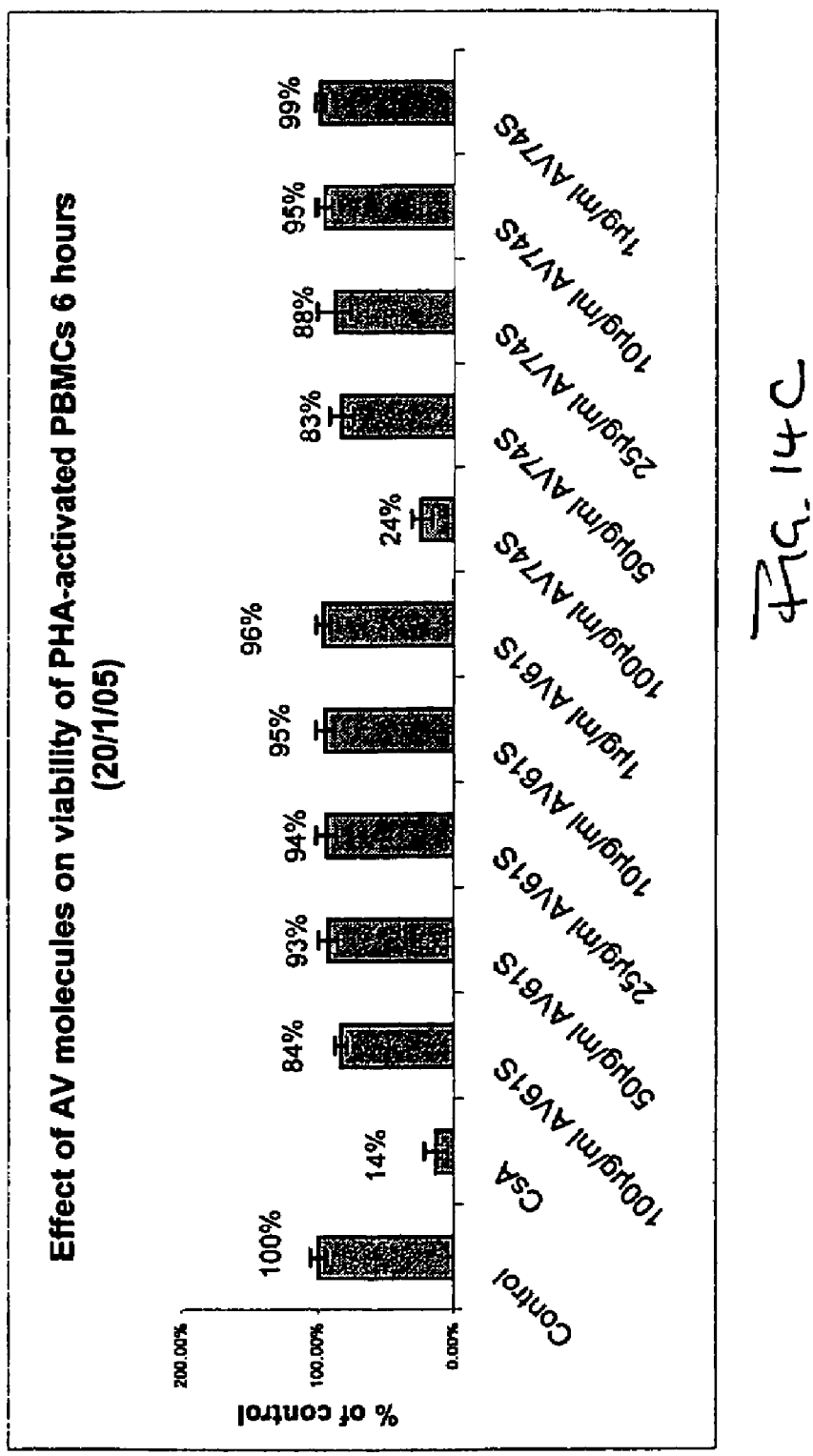

Example 9 was repeated, except that the cells were incubated for 48 hours prior to dyeing with Alamar Blue. The results are shown in FIGS. 14A-14C.

As shown in FIGS. 13A-13C and FIGS. 14A-14C, Alamar Blue dyeing confirmed the non-toxic effect of the molecules, except for AV 74S at 100 μg/ml which has the same activity and toxicity pattern as Cyclosporine (CsA). All other concentrations with AV 61S and AV 74S showed an anti-proliferative effect.

Example 13

Toxicity of AV Compounds Against PBMC Cells by Trypan Blue Reagent

Figure 15A:
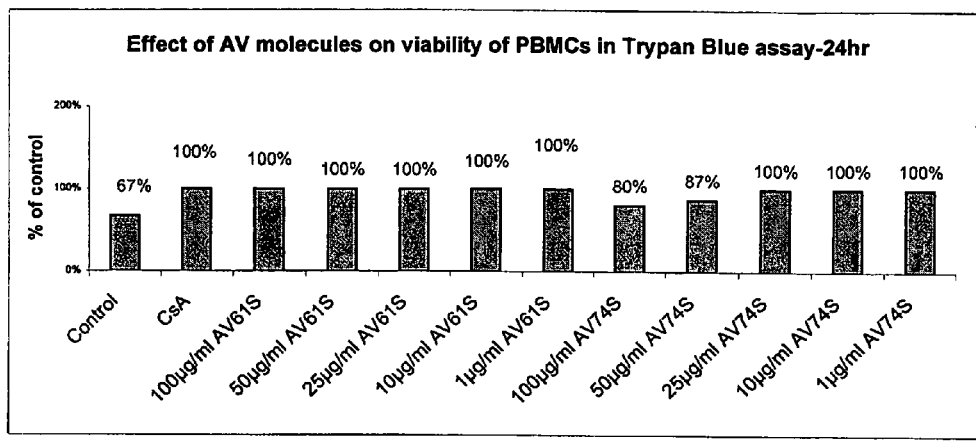
Figure 15B:
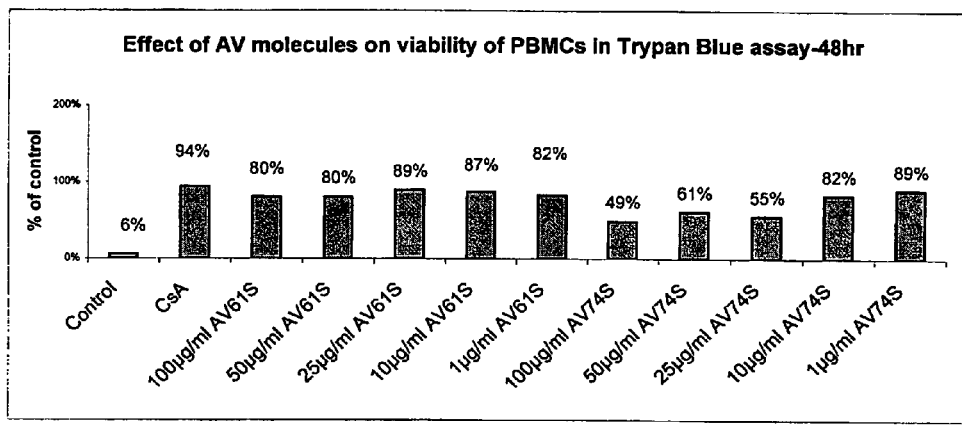

Examples 11 and 12 were repeated using, in each case, Trypan Blue reagent instead of Alamar Blue. The results, which confirm those obtained using Alamar Blue, are shown in FIGS. 15A and 15B respectively.

EQUIVALENTS

Those skilled in the art will recognize, or be able to ascertain using no more than routine experimentation, numerous equivalents to the specific procedures described herein. Such equivalents are considered to be within the scope of the invention. Various substitutions, alterations, and modifications may be made to the invention without departing from the spirit and scope of the invention. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

What is claimed is:

1. A compound of formula A', B', D', or E':

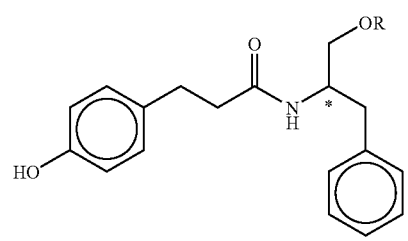

Formula A'

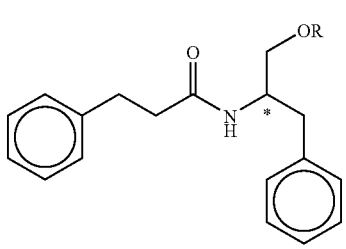

Formula B'

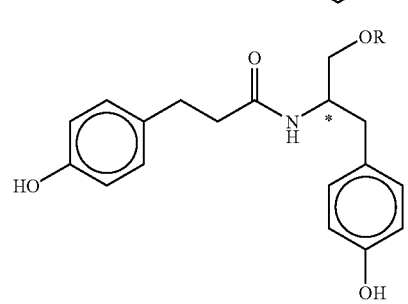

Formula D'

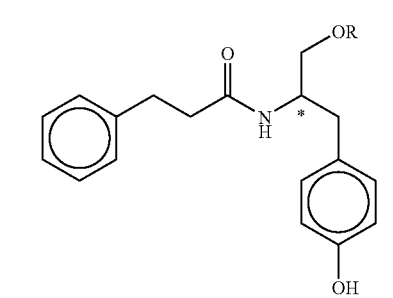

Formula E' wherein the chiral centre indicated by * is in the S-enantiomeric conformation, and R represents a polyalkylene glycol polymer having p units, in which p is an integer from 1-100.

2. The compound of claim 1, wherein R is polyethylene glycol or polypropylene glycol.

3. The compound of claim 1, wherein p is an integer in the range 1 to 20.

4. The compound of claim 1, wherein p is 7.

5. The compound of claim 1, wherein p is 17.

6. A compound wherein the compound is (S) 2-N (3-O-polypropyleneglycol) propylbenzene)-3-(4-hydroxyphenyl) propylamide (p=7).

7. A compound wherein the compound is (S) 2-N (3-O-(polypropyleneglycol)-1-propyl-4-hydroxybenzene)-3-phenylpropylamide (p=7).

8. A composition comprising at least 20% wt. of a compound of claim 5, and a pharmaceutically acceptable carrier.

9. The composition of claim 8, further comprising unreacted polyalkylene glycol as a side product.

10. The composition of claim 8, wherein said composition comprises more than about 30% wt. said compound.

11. The composition of claim 8, wherein said composition comprises more than about 40% wt. said compound.

12. The composition of claim 8, wherein said composition comprises more than about 75% wt. said compound.

13. The compound of claim 1, wherein p is 34.

14. The compound of claim 1, wherein p is 69.

15. The compound of claim 1, wherein p is 1.

16. The compound of claim 1, wherein p is 12.

17. A compound of formula E':

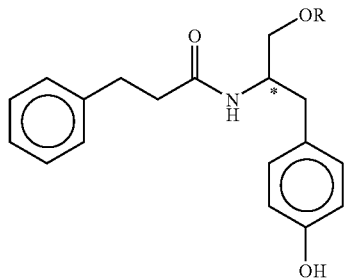

wherein the chiral center indicated by the * is in the S-enantiomeric configuration and R represents a polyethylene glycol polymer having p units, wherein p is 1.

18. A compound of formula E':

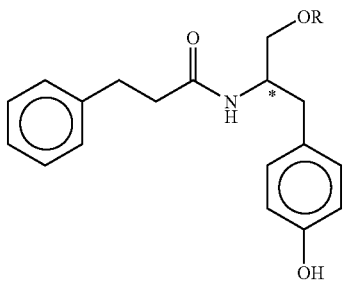

wherein the chiral center indicated by the * is in the S-enantiomeric configuration and R represents a polyethylene glycol polymer having p units, wherein p is 2.

19. A pharmaceutical composition comprising a compound of claim 1 and one or more pharmaceutically acceptable excipients.

* * * * *